United States Patent
Kishalay et al.

(10) Patent No.: US 9,587,033 B2
(45) Date of Patent: Mar. 7, 2017

(54) THERAPEUTIC AND DIAGNOSTIC APPLICATIONS TARGETING TNK-1

(75) Inventors: Hoare Kishalay, Gainesville, FL (US); William Stratford May, Gainesville, FL (US); Sarasija Hoare, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 567 days.

(21) Appl. No.: 13/885,340

(22) PCT Filed: Nov. 15, 2011

(86) PCT No.: PCT/US2011/060738
§ 371 (c)(1),
(2), (4) Date: Jul. 29, 2013

(87) PCT Pub. No.: WO2012/068073
PCT Pub. Date: May 24, 2012

(65) Prior Publication Data
US 2013/0302341 A1    Nov. 14, 2013

Related U.S. Application Data

(60) Provisional application No. 61/413,672, filed on Nov. 15, 2010.

(51) Int. Cl.
*A61K 39/00* (2006.01)
*C07K 16/40* (2006.01)
*A61K 39/395* (2006.01)

(52) U.S. Cl.
CPC ............ *C07K 16/40* (2013.01); *A61K 39/395* (2013.01); *A61K 2039/5152* (2013.01); *C07K 2317/34* (2013.01); *G01N 2333/9121* (2013.01)

(58) Field of Classification Search
CPC .. G01N 33/574; C07K 14/705; A61K 39/395; A61K 2039/5152
USPC ................ 435/7.1, 7.23; 530/387.7
See application file for complete search history.

(56) References Cited

U.S. PATENT DOCUMENTS

| | | |
|---|---|---|
| 2008/0051318 A1 | 2/2008 | Li et al. |
| 2008/0292546 A1 | 11/2008 | Clarke et al. |
| 2009/0047675 A1 | 2/2009 | Roberts et al. |
| 2010/0062951 A1 | 3/2010 | Khvorova et al. |
| 2010/0093727 A1 | 4/2010 | Xi |
| 2010/0113458 A1 | 5/2010 | Fink et al. |
| 2010/0137144 A1 | 6/2010 | Remacle et al. |
| 2010/0151495 A9 | 6/2010 | Polakiewicz et al. |
| 2010/0152434 A1 | 6/2010 | Peterson |
| 2010/0183610 A1 | 7/2010 | Li et al. |
| 2010/0266580 A1 | 10/2010 | Gu |

FOREIGN PATENT DOCUMENTS

| | | |
|---|---|---|
| WO | 2008066498 | 6/2008 |
| WO | 2009075825 A2 | 6/2009 |
| WO | 2009148628 A2 | 12/2009 |

OTHER PUBLICATIONS

Felschow et al. (Biochem. Biophys. Res. Commun. Jun. 24, 2000; 273 (1): 294-301).*
Hoare et al. (Cancer Res. Nov. 1, 2008; 68 (21): 8723-32).*
Gu, T. et al., "Identification of activated Tnk1 kinase in Hodgkin's lymphoma", Leukemia, 2010, vol. 24, No. 4, pp. 861-865.
Azoitei, N. et al., "Thirty-eight-negative kinase 1 (TNK1) facilitates TNF-induced apoptosis by blocking Nf-B activation", Oncogene, 2007, vol. 26, pp. 6536-6545.
Felschow, D. M. et al., "Characterization of the tyrosine kinase Tnk1 and its binding with phospholipase C-γ1", Biochem Biophys Res Commun, 2000, vol. 273, pp. 294-301.
Lierman, E. et al., "Identification of protein tyrosine kinases with oncogenic potential using a retroviral insertion mutagenesis screen", Haematologica, 2009, vol. 94, No. 10, pp. 1440-1444.

* cited by examiner

*Primary Examiner* — Stephen Rawlings
(74) *Attorney, Agent, or Firm* — Timothy H. Van Dyke; Beusse, Wolter, Sanks & Maire PLLC

(57) ABSTRACT

Disclosed herein are novel antibodies specific to Tnk1 or variants thereof. Also disclosed are methods of using such antibodies. The methods include therapeutic methods against certain types of cancers or infections involving administration of novel antibodies or fragments thereof. Also, methods of using highly selective antibodies for detecting aberrant Tnk1 or functionally deficient Tnk1.

4 Claims, 3 Drawing Sheets

THERAPEUTIC AND DIAGNOSTIC APPLICATIONS TARGETING TNK-1

CROSS-REFERENCE TO RELATED APPLICATIONS

This application is related to U.S. Provisional Application No. 61/413,672; filed Nov. 15, 2010, to which priority is claimed under 35 USC 119, and which is incorporated herein in its entirety.

SEQUENCE LISTING

The instant application contains a Sequence Listing which has been submitted in ASCII format via EFS-Web and is hereby incorporated by reference in its entirety. Said ASCII copy, is named 10457181US sequencelisting.txt.

BACKGROUND

Tnk1 is a non-receptor protein tyrosine kinase with a putative size of 72 kDa, and is a member of ACK-tyrosine kinase family. It is related to the Ack1 (TNK2) non-receptor kinase that binds to cdc42 and inhibits its GTPase activity. The catalytic domain of TNK1 is located at the N terminus followed by a SH3 domain and a proline rich region. Tnk1 is expressed in core blood, bone marrow, and leukemia cell lines (see Hoehn et al, Oncogene. 12(4):903-13 (1996)). Tnk1 interacts with Phospholipase C gamma (PLC-g). It facilitates TNF alpha-induced apoptosis by blocking NF-kB activation (see Felschow et al., Biochem Biophys Res Commun 73(1):294-301 (2000); Azoieti et al., Oncogene. (2007) 26:6536-6545). Active TNK1 may play a role in regulating cell death by preventing TNF-a induced NF-kB transactivation (Azoieti et al., Oncogene. (2007) 26:6536-6545).

Tnk1/Kos1 is a tumor suppressor in both human and mouse. Loss of Tnk1/kos1 in mice results in the spontaneous development of tumors namely diffuse large B-cell lymphomas (DLBCL), hepatocellular carcinomas, adenocarcinomas of lung, etc. Apart from the loss of human Tnk1 protein in a cohort of patients with DLBCL, the inventors have now realized that over expression of a 60 kDa truncated Tnk1 fusion gene product has been found in a patient with Hodgkin Lymphoma and in other cancers. The truncated Tnk1 protein though tyrosine phosphorylated is oncogenic because it is kinase dead and associated with increased Ras-MAPK activities. To date, effective Tnk1-Kos1 antibodies are not commercially available.

DETAILED DESCRIPTION

Figure 1:
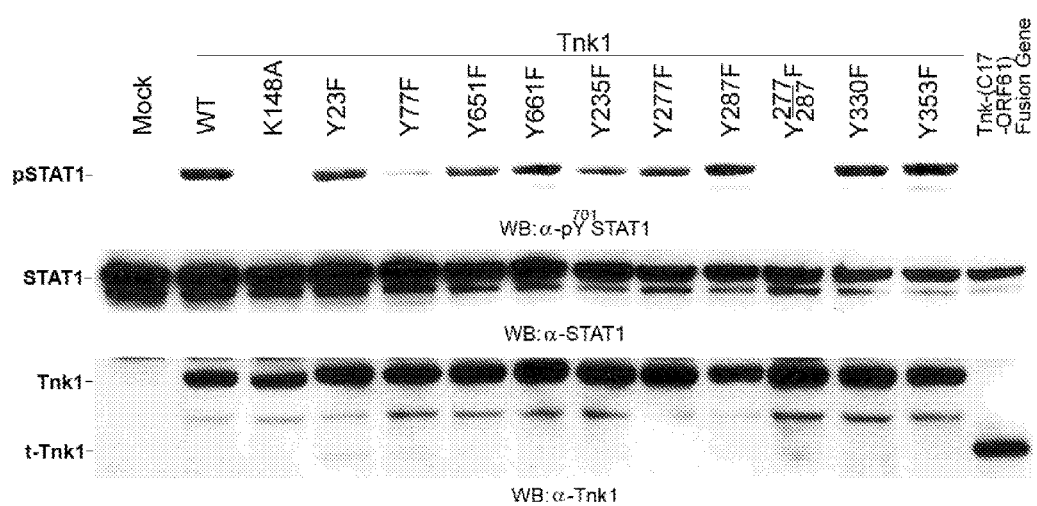
FIG. 1: Tnk1's tyrosine residue (s) are critical for its PTK activity. Tnk1 contains 9 tyrosine (Y) residues of which 5 reside in its kinase domain while 2 each resides in its N-terminal and C-terminal domains. To determine the impact of each Y residue in Tnk1 towards its auto-kinase activity or on its substrates (STAT1 and Grb2), we replaced individually the nine tyrosine residues with phenylalanine (F) and compared the protein tyrosine kinase activities of the mutants with wt Tnk1. Cos7 cells were transfected with Tnk1 mutants and their effect was determined by analyzing cell lysate (100 μg protein) by Western blotting (WB). Like the kinase-dead Tnk1 K148A or Y277/287 mutant, t-Tnk1 fails to Y-phosphorylate STAT1, while Tnk1 Y77F and Y235F mutants show dramatic reduction in STAT1 Y-phosphorylation.

Tnk1 is a 666 amino acid ubiquitously expressed protein tyrosine kinase that functions as a tumor suppressor to maintain cellular homeostasis (1, 2, 3). Knockout of TNK1 gene in mice by homologous recombination spontaneously gives rise to different types of cancers upon aging (1, 4). Hence, therapeutic and diagnostic applications targeting Tnk1 is an ideal choice for the development of marketable products. We have developed two antibodies (A and B) against specific sites in Tnk1 that are critical for the function of Tnk1. Results and discussion below will reveal the critical importance of the two antibodies for therapeutic and diagnostics of cancer, in general.

Due to the growing importance of Tnk1/Kos1 in cancer, a novel Tnk1 antibodies have been developed and generated as described below. In one embodiment, an antibody according to the present invention is developed against a specific N-terminal sequence (EHKEPTLPSDSPRHLPE, SEQ ID NO. 1), and specifically recognizes wild type Tnk1 and the 60 KDa tTnk1 but not Kos1. Since full length Tnk1 functions as tumor suppressor while tTnk1 functions as a potential oncogene, this highly specific antibody will help identify the presence or loss of Tnk1 from cells. The anti-Tnk1 (N-terminal) efficiently immunoprecipitates tTnk1 and has identified plasma cells in normal lymph nodes expressing Tnk1 by immunohistochemistry. The antibody is efficient for Western Blotting.

According to another embodiment, the present invention is directed to an antibody developed against a specific C-terminal sequence (RERLPWPKRKPPHNHPMG, SEQ ID NO. 2), Antibody B, and specifically recognizes wild type Tnk1 but not Kos1 and the 60 KDa tTnk1. Since full length Tnk1 functions as tumor suppressor while tTnk1 functions as a potential oncogene, this highly specific antibody will help identify the presence or loss of Tnk1 from cells.

In a further embodiment, the present invention is directed to an antibody developed against a specific phospho-tyrosine (Y77) residue of Tnk1/Kos1, which is believed to play a role in the regulation of Ras activity. The specific peptide against which this antibody is developed is KNWVYpKILG-GFAPEHKE (SEQ ID NO. 3). The Y77-Tnk1 antibody, Antibody A, specifically recognizes wild type Tnk1, Kos1 and the tTnk1 via Western Blotting. It can efficiently immuno-precipitate wild type Tnk1, Kos1 and the tTnk1, and does not block or suppress the tyrosine kinase activity of Tnk1/Kos1 proteins. Furthermore, the antibody has been found to detect Y77-phosphorylated Tnk1 in a specific subset of cells within germinal center of human lymph nodes by immuno histo-chemical (IHC) technique. Interestingly, the inventors have discovered that in patient specimens (B-cell lymphomas) that the anti C-ter Tnk1 antibody (Seq ID No2) can detect full length Tnk1 (72 kDa) by IHC while the anti-pY77 Tnk1 antibody (Seq ID No3) fails to detect Tnk1 in the same specimens. This indicates absence of functionally active phosphorylated-Tnk1 in patient specimens (B-cell lymphomas).

In yet another aspect, the invention provides a method for detecting a Tnk1 related proteins (TRP) such as wild-type TNK1 protein, an aberrantly phosphorylated Tnk1 protein, a Tnk1-C17ORF61 fusion polypeptide (or tTnk1). The method involves adding an antibody of the present invention to a sample comprising the TRP under conditions that permit the specific binding of said antibody to the TRP, and detecting binding of said antibody. Another method embodiment pertains to a method for quantifying the amount of a TRP selected from the group consisting of a wild-type Tnk1 protein, an aberrantly phosphorylated Tnk1 protein, and/or a Tnk1-C17ORF61 fusion polypeptide in a sample using a phosphorylatable labeled peptide comprising SEQ ID NO. 3 as an internal standard.

Another method embodiment pertains to a method for detecting the presence of aberrantly expressed Tnk1 in a cancer. The method involves contacting a biological sample of said cancer with an antibody of the invention, wherein binding of said antibody to said biological sample indicates the presence of said aberrantly expressed Tnk1 in said cancer. In some embodiments, the antibody specifically binds SEQ ID NO. 1, 2, or 3. In some embodiments, the aberrantly expressed Tnk1 is selected from the group consisting of an aberrantly phosphorylated Tnk1 protein, a TNK1-C17ORF61 fusion polypeptide and/or another form of a truncated TNK1 polypeptide. In some embodiments, the cancer is from a patient (e.g., a human patient). In some embodiments, the cancer is lymphoma (e.g., Hodgkin's lymphoma (HL)). In some embodiments, the presence of aberrantly expressed Tnk1 in said cancer identifies said cancer as likely to respond to a composition comprising at least one Tnk1 kinase-inhibiting therapeutic. In some embodiments, the method is implemented in a flow-cytometry (FC), immuno-histochemistry (IHC), or immuno-fluorescence (IF) assay format. In some embodiments, the activity of said aberrantly expressed Tnk1 is detected.

In further aspects, the invention provides methods for making Tnk1 site-specific antibodies, and provides compositions comprising a peptide, protein, or antibody of the invention, including pharmaceutical compositions. In a further aspect, the invention provides methods of treating or preventing carcinoma and/or leukemia in a subject, wherein the carcinoma and/or leukemia is associated with the phosphorylation state of a phosphorylation site of Tnk1. In certain embodiments, the methods comprise administering to a subject a therapeutically effective amount of an antibody or antigen-binding fragment thereof that specifically binds at a specific site of Tnk1, denoted by SEQ ID NO. 1, 2, or 3. In a further aspect, the invention provides methods for detecting and quantitating phosphorylation at a novel tyrosine phosphorylation site of the invention.

Also provided are pharmaceutical compositions and kits comprising one or more antibodies or peptides of the invention and methods of using them.

Antibodies

An antibody of the invention can be an intact, four immunoglobulin chain antibody comprising two heavy chains and two light chains. The heavy chain of the antibody can be of any isotype including IgM, IgG, IgE, IgG, IgA or IgD or sub-isotype including IgG1, IgG2, IgG3, IgG4, IgE1, IgE2, etc. The light chain can be a kappa light chain or a lambda light chain.

Also within the invention are antibody molecules with fewer than 4 chains, including single chain antibodies, Camelid antibodies and the like and components of the antibody, including a heavy chain or a light chain. The term "antibody" (or "antibodies") refers to all types of immunoglobulins. The term "an antigen-binding fragment of an antibody" refers to any portion of an antibody that retains specific binding of the intact antibody. An exemplary antigen-binding fragment of an antibody is the heavy chain and/or light chain CDR, or the heavy and/or light chain variable region. The term "does not bind," when appeared in context of an antibody's binding to one phospho-form (e.g., phosphorylated form) of a sequence, means that the antibody does not substantially react with the other phospho-form (e.g., non-phosphorylated form) of the same sequence. One of skill in the art will appreciate that the expression may be applicable in those instances when (1) a phospho-specific antibody either does not apparently bind to the non-phospho form of the antigen as ascertained in commonly used experimental detection systems (Western blotting, IHC, Immunofluorescence, etc.); (2) where there is some reactivity with the surrounding amino acid sequence, but that the phosphorylated residue is an immunodominant feature of the reaction. In cases such as these, there is an apparent difference in affinities for the two sequences. Dilutional analyses of such antibodies indicates that the antibodies apparent affinity for the phosphorylated form is at least 10-100 fold higher than for the non-phosphorylated form; or where (3) the phospho-specific antibody reacts no more than an appropriate control antibody would react under identical experimental conditions. A control antibody preparation might be, for instance, purified immunoglobulin from a pre-immune animal of the same species, an isotype- and species-matched monoclonal antibody. Tests using control antibodies to demonstrate specificity are recognized by one of skill in the art as appropriate and definitive.

In some embodiments an immunoglobulin chain may comprise in order from 5' to 3', a variable region and a constant region. The variable region may comprise three complementarity determining regions (CDRs), with interspersed framework (FR) regions for a structure FR1, CDR1, FR2, CDR2, FR3, CDR3 and FR4. Also within the invention are heavy or light chain variable regions, framework regions and CDRs. An antibody of the invention may comprise a heavy chain constant region that comprises some or all of a CH1 region, hinge, CH2 and CH3 region.

An antibody of the invention may have a binding affinity ($K_D$) of $1 \times 10^{-7}$ M or less. In other embodiments, the antibody binds with a $K_D$ of $1 \times 10^{-8}$ M, $1 \times 10^{-9}$ M, $1 \times 10^{-10}$ M, $1 \times 10^{-11}$ M, $1 \times 10^{-12}$ M or less. In certain embodiments, the $K_D$ is 1 pM to 500 pM, between 500 pM to 1 µM, between 1 µM to 100 nM, or between 100 mM to 10 nM.

Antibodies of the invention can be derived from any species of animal, such as a mammal. Non-limiting exemplary natural antibodies include antibodies derived from human, chicken, goats, and rodents (e.g., rats, mice, hamsters and rabbits), including transgenic rodents genetically engineered to produce human antibodies (see, e.g., Lonberg et al., WO93/12227; U.S. Pat. No. 5,545,806; and Kucherlapati, et al., WO91/10741; U.S. Pat. No. 6,150,584, which are herein incorporated by reference in their entirety). Natural antibodies are the antibodies produced by a host animal. "Genetically altered antibodies" refer to antibodies wherein the amino acid sequence has been varied from that of a native antibody. Because of the relevance of recombinant DNA techniques to this application, one need not be confined to the sequences of amino acids found in natural antibodies; antibodies can be redesigned to obtain desired characteristics. The possible variations are many and range from the changing of just one or a few amino acids to the complete redesign of, for example, the variable or constant region. Changes in the constant region will, in general, be made in order to improve or alter characteristics, such as complement fixation, interaction with membranes and other effector functions. Changes in the variable region will be made in order to improve the antigen binding characteristics.

Antibodies disclosed in the invention may be polyclonal or monoclonal. As used herein, the term "epitope" refers to the smallest portion of a protein capable of selectively binding to the antigen binding site of an antibody. It is well accepted by those skilled in the art that the minimal size of a protein epitope capable of selectively binding to the antigen binding site of an antibody is about five or six to seven amino acids.

Other antibodies specifically contemplated are oligoclonal antibodies. As used herein, the phrase "oligoclonal antibodies" refers to a predetermined mixture of distinct monoclonal antibodies. See, e.g., PCT publication WO 95/20401; U.S. Pat. Nos. 5,789,208 and 6,335,163. In one embodiment, oligoclonal antibodies consisting of a predetermined mixture of antibodies against one or more epitopes are generated in a single cell. In other embodiments, oligoclonal antibodies comprise a plurality of heavy chains capable of pairing with a common light chain to generate antibodies with multiple specificities (e.g., PCT publication WO 04/009618). Oligoclonal antibodies are useful for targeting multiple epitopes on a single target molecule. In view of the assays and epitopes disclosed herein, those skilled in the art can generate or select antibodies or mixtures of antibodies that are applicable for an intended purpose and desired need.

Recombinant antibodies against the phosphorylation sites identified in the invention are also included in the present application. These recombinant antibodies have the same amino acid sequence as the natural antibodies or have altered amino acid sequences of the natural antibodies in the present application. They can be made in any expression systems including both prokaryotic and eukaryotic expression systems or using phage display methods (see, e.g., Dower et al., WO91/17271 and McCafferty et al., WO92/01047; U.S. Pat. No. 5,969,108, which are herein incorporated by reference in their entirety).

Antibodies can be engineered in numerous ways. They can be made as single-chain antibodies (including small modular immunopharmaceuticals or SMIPs™), Fab and F(ab')$_2$ fragments, etc. Antibodies can be humanized, chimerized, deimmunized, or fully human. Numerous publications set forth the many types of antibodies and the methods of engineering such antibodies. For example, see U.S. Pat. Nos. 6,355,245; 6,180,370; 5,693,762; 6,407,213; 6,548,640; 5,565,332; 5,225,539; 6,103,889; and 5,260,203.

The genetically altered antibodies should be functionally equivalent to the above-mentioned natural antibodies. In certain embodiments, modified antibodies provide improved stability or/and therapeutic efficacy. Examples of modified antibodies include those with conservative substitutions of amino acid residues, and one or more deletions or additions of amino acids that do not significantly deleteriously alter the antigen binding utility. Substitutions can range from changing or modifying one or more amino acid residues to complete redesign of a region as long as the therapeutic utility is maintained. Antibodies of this application can be modified post-translationally (e.g., acetylation, and/or phosphorylation) or can be modified synthetically (e.g., the attachment of a labeling group).

Antibodies with engineered or variant constant or Fc regions can be useful in modulating effector functions, such as, for example, antigen-dependent cytotoxicity (ADCC) and complement-dependent cytotoxicity (CDC). Such antibodies with engineered or variant constant or Fc regions may be useful in instances where a parent singling protein (SEQ ID NOS. 1-3) is expressed in normal tissue; variant antibodies without effector function in these instances may elicit the desired therapeutic response while not damaging normal tissue. Accordingly, certain aspects and methods of the present disclosure relate to antibodies with altered effector functions that comprise one or more amino acid substitutions, insertions, and/or deletions.

In certain embodiments, genetically altered antibodies are chimeric antibodies and humanized antibodies.

The chimeric antibody is an antibody having portions derived from different antibodies. For example, a chimeric antibody may have a variable region and a constant region derived from two different antibodies. The donor antibodies may be from different species. For example, the variable region of a chimeric antibody is non-human, e.g., murine, and the constant region is human.

The genetically altered antibodies used in the invention include CDR grafted humanized antibodies. In one embodiment, the humanized antibody comprises heavy and/or light chain CDRs of a non-human donor immunoglobulin and heavy chain and light chain frameworks and constant regions of a human acceptor immunoglobulin. The method of making humanized antibody is disclosed in U.S. Pat. Nos. 5,530,101; 5,585,089; 5,693,761; 5,693,762; and 6,180,370 each of which is incorporated herein by reference in its entirety.

Antigen-binding fragments of the antibodies of the invention, which retain the binding specificity of the intact antibody, are also included in the invention. Examples of these antigen-binding fragments include, but are not limited to, partial or full heavy chains or light chains, variable regions, or CDR regions of any Tnk1 site-specific antibodies described herein. In one embodiment of the application, the antibody fragments are truncated chains (truncated at the carboxyl end). In certain embodiments, these truncated chains possess one or more immunoglobulin activities (e.g., complement fixation activity). Examples of truncated chains include, but are not limited to, Fab fragments (consisting of the VL, VH, CL and CH1 domains); Fd fragments (consisting of the VH and CH1 domains); Fv fragments (consisting of VL and VH domains of a single chain of an antibody); dAb fragments (consisting of a VH domain); isolated CDR regions; (Fab')$_2$ fragments, bivalent fragments (comprising two Fab fragments linked by a disulphide bridge at the hinge region). The truncated chains can be produced by conventional biochemical techniques, such as enzyme cleavage, or recombinant DNA techniques, each of which is known in the art. These polypeptide fragments may be produced by proteolytic cleavage of intact antibodies by methods well known in the art, or by inserting stop codons at the desired locations in the vectors using site-directed mutagenesis, such as after CH1 to produce Fab fragments or after the hinge region to produce (Fab')$_2$ fragments. Single chain antibodies may be produced by joining VL- and VH-coding regions with a DNA that encodes a peptide linker connecting the VL and VH protein fragments Papain digestion of antibodies produces two identical antigen-binding fragments, called "Fab" fragments, each with a single antigen-binding site, and a residual "Fc" fragment, whose name reflects its ability to crystallize readily. Pepsin treatment of an antibody yields an F(ab')$_2$ fragment that has two antigen-combining sites and is still capable of cross-linking antigen. "Fv" usually refers to the minimum antibody fragment that contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the CDRs confer antigen-binding specificity to the antibody. However, even a single variable domain (or half of an Fv comprising three CDRs specific for an antigen) has the ability to recognize and bind antigen, although likely at a lower affinity than the entire binding site.

Thus, in certain embodiments, the antibodies of the application may comprise 1, 2, 3, 4, 5, 6, or more CDRs that recognize the sites pertaining to SEQ ID NOs 1-3.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments that have hinge cysteines between them. Other chemical couplings of antibody fragments are also known.

"Single-chain Fv" or "scFv" antibody fragments comprise the $V_H$ and $V_L$ domains of an antibody, wherein these domains are present in a single polypeptide chain. In certain embodiments, the Fv polypeptide further comprises a polypeptide linker between the $V_H$ and $V_L$ domains that enables the scFv to form the desired structure for antigen binding. For a review of scFv see Pluckthun in The Pharmacology of Monoclonal Antibodies, vol. 113, Rosenburg and Moore, eds. (Springer-Verlag: New York, 1994), pp. 269-315.

SMIPs are a class of single-chain peptides engineered to include a target binding region and effector domain (CH2 and CH3 domains). See, e.g., U.S. Patent Application Publication No. 20050238646. The target binding region may be derived from the variable region or CDRs of an antibody, e.g., a Tnk1 site-specific antibody of the application. Alternatively, the target binding region is derived from a protein that binds a phosphorylation site. Bispecific antibodies may be monoclonal, human or humanized antibodies that have binding specificities for at least two different antigens. In the present case, one of the binding specificities is for the specific site, the other one is for any other antigen, such as for example, a cell-surface protein or receptor or receptor subunit. Alternatively, a therapeutic agent, such as a drug, toxin, enzyme, DNA, or radionucleotide, may be placed on one arm. In some embodiments, the antigen-binding fragment can be a diabody.

The term "diabody" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90: 6444-6448 (1993).

Camelid antibodies refer to a unique type of antibodies that are devoid of light chain, initially discovered from animals of the camelid family. The heavy chains of these so-called heavy-chain antibodies bind their antigen by one single domain, the variable domain of the heavy immunoglobulin chain, referred to as VHH. VHHs show homology with the variable domain of heavy chains of the human VHIII family. The VHHs obtained from an immunized camel, dromedary, or llama have a number of advantages, such as effective production in microorganisms such as *Saccharomyces cerevisiae*.

In certain embodiments, single chain antibodies, and chimeric, humanized or primatized (CDR-grafted) antibodies, as well as chimeric or CDR-grafted single chain antibodies, comprising portions derived from different species, are also encompassed by the present disclosure as antigen-binding fragments of an antibody. The various portions of these antibodies can be joined together chemically by conventional techniques, or can be prepared as a contiguous protein using genetic engineering techniques. For example, nucleic acids encoding a chimeric or humanized chain can be expressed to produce a contiguous protein. See, e.g., U.S. Pat. Nos. 4,816,567 and 6,331,415; U.S. Pat. No. 4,816,397; European Patent No. 0,120,694; WO 86/01533; European Patent No. 0,194,276 B1; U.S. Pat. No. 5,225,539; and European Patent No. 0,239,400 B1. See also, Newman et al., BioTechnology, 10: 1455-1460 (1992), regarding primatized antibody. See, e.g., Ladner et al., U.S. Pat. No. 4,946,778; and Bird et al., Science, 242: 423-426 (1988)), regarding single chain antibodies. In addition, functional fragments of antibodies, including fragments of chimeric, humanized, primatized or single chain antibodies, can also be produced. Functional fragments of the subject antibodies retain at least one binding function and/or modulation function of the full-length antibody from which they are derived. Since the immunoglobulin-related genes contain separate functional regions, each having one or more distinct biological activities, the genes of the antibody fragments may be fused to functional regions from other genes (e.g., enzymes, U.S. Pat. No. 5,004,692, which is incorporated by reference in its entirety) to produce fusion proteins or conjugates having novel properties. Non-immunoglobulin binding polypeptides are also contemplated. For example, CDRs from an antibody disclosed herein may be inserted into a suitable non-immunoglobulin scaffold to create a non-immunoglobulin binding polypeptide. Suitable candidate scaffold structures may be derived from, for example, members of fibronectin type III and cadherin superfamilies.

Also contemplated are other equivalent non-antibody molecules, such as protein binding domains or aptamers, which bind, in a phospho-specific manner, to an amino acid sequence comprising a novel phosphorylation site of the invention. See, e.g., Neuberger et al, Nature 312: 604 (1984). Aptamers are oligonucleic acid or peptide molecules that bind a specific target molecule. DNA or RNA aptamers are typically short oligonucleotides, engineered through repeated rounds of selection to bind to a molecular target. Peptide aptamers typically consist of a variable peptide loop attached at both ends to a protein scaffold. This double structural constraint generally increases the binding affinity of the peptide aptamer to levels comparable to an antibody (nanomolar range). The invention also discloses the use of the phosphorylation site-specific antibodies with immunotoxins. Conjugates that are immunotoxins including antibodies have been widely described in the art. The toxins may be coupled to the antibodies by conventional coupling techniques or immunotoxins containing protein toxin portions can be produced as fusion proteins. In certain embodiments, antibody conjugates may comprise stable linkers and may release cytotoxic agents inside cells (see U.S. Pat. Nos. 6,867,007 and 6,884,869). The conjugates of the present application can be used in a corresponding way to obtain such immunotoxins. Illustrative of such immunotoxins are those described by Byers et al., Seminars Cell Biol 2:59-70 (1991) and by Fanger et al, Immunol Today 12:51-54 (1991). Exemplary immunotoxins include radiotherapeutic agents, ribosome-inactivating proteins (RIPs), chemotherapeutic agents, toxic peptides, or toxic proteins.

Accordingly, antibodies or fragments thereof can be produced that are specific to SEQ ID NOs 1, 2 and/or 3.

The Tnk1 site-specific antibodies disclosed in the invention may be used singly or in combination. The antibodies may also be used in an array format for high throughput uses. An antibody microarray is a collection of immobolized antibodies, typically spotted and fixed on a solid surface (such as glass, plastic and silicon chip).

In another aspect, the antibodies of the invention modulate at least one, or all, biological activities of a parent protein. The biological activities of a parent protein include: 1) ligand binding activities (for instance, these neutralizing antibodies may be capable of competing with or completely blocking the binding of a parent signaling protein to at least one, or all, of its ligands; 2) signaling transduction activities, such as receptor dimerization, or tyrosine phosphorylation; and 3) cellular responses induced by a parent signaling protein, such as oncogenic activities (e.g., cancer cell proliferation mediated by a parent signaling protein), and/or angiogenic activities.

In certain embodiments, the antibodies of the invention may have at least one activity selected from the group consisting of: 1) inhibiting cancer cell growth or proliferation; 2) inhibiting cancer cell survival; 3) inhibiting angiogenesis; 4) inhibiting cancer cell metastasis, adhesion, migration or invasion; 5) inducing apoptosis of cancer cells; 6) incorporating a toxic conjugate; and 7) acting as a diagnostic marker.

In certain embodiments, the Tnk1 site specific antibodies disclosed in the invention are especially indicated for diagnostic and therapeutic applications as described herein. Accordingly, the antibodies may be used in therapies, including combination therapies, in the diagnosis and prognosis of disease, as well as in the monitoring of disease progression. The invention, thus, further includes compositions comprising one or more embodiments of an antibody or an antigen binding portion of the invention as described herein. The composition may further comprise a pharmaceutically acceptable carrier. The composition may comprise two or more antibodies or antigen-binding portions, each with specificity for a different site of the invention or two or more different antibodies or antigen-binding portions all of which are specific for the same site of the invention. A composition of the invention may comprise one or more antibodies or antigen-binding portions of the invention and one or more additional reagents, diagnostic agents or therapeutic agents.

The present application provides for the polynucleotide molecules encoding the antibodies and antibody fragments and their analogs described herein. Because of the degeneracy of the genetic code, a variety of nucleic acid sequences encode each antibody amino acid sequence. The desired nucleic acid sequences can be produced by de novo solid-phase DNA synthesis or by PCR mutagenesis of an earlier prepared variant of the desired polynucleotide. In one embodiment, the codons that are used comprise those that are typical for human or mouse (see, e.g., Nakamura, Y., Nucleic Acids Res. 28: 292 (2000)).

Production of Antibodies

The invention also provides immortalized cell lines that produce an antibody of the invention. For example, hybridoma clones, constructed as described above, that produce monoclonal antibodies to the sites disclosed herein are also provided. Similarly, the invention includes recombinant cells producing an antibody of the invention, which cells may be constructed by well known techniques; for example the antigen combining site of the monoclonal antibody can be cloned by PCR and single-chain antibodies produced as phage-displayed recombinant antibodies or soluble antibodies in *E. coli* {see, e.g., ANTIBODY ENGINEERING PROTOCOLS, 1995, Humana Press, Sudhir Paul editor.)

In another aspect, the invention provides a method for making Tnk1 site-specific antibodies. Polyclonal antibodies of the invention may be produced according to standard techniques by immunizing a suitable animal {e.g., rabbit, goat, etc.) with an antigen comprising a novel site of the invention, (i.e. SEQ ID NOs. 1-3) in either the phosphorylated or unphosphorylated state, depending upon the desired specificity of the antibody, collecting immune serum from the animal, and separating the polyclonal antibodies from the immune serum, in accordance with known procedures and screening and isolating a polyclonal antibody specific for the novel site of interest as further described below. Methods for immunizing non-human animals such as mice, rats, sheep, goats, pigs, cattle and horses are well known in the art. See, e.g., Harlow and Lane, Antibodies: A Laboratory Manual, New York: Cold Spring Harbor Press, 1990.

The immunogen may be the full length protein or a peptide comprising the novel site of interest. In some embodiments the immunogen is a peptide of from 7 to 20 amino acids in length, or from about 8 to 17 amino acids in length. In particular, the peptide is at least a 7 amino acid portion of SEQ ID NOs. 1-3. In some embodiments, the peptide antigen will comprise about 3 to 8 amino acids on each side of the phosphorylatable tyrosine. In yet other embodiments, the peptide antigen may comprise four or more amino acids flanking each side of the phosphorylatable amino acid and encompassing it. Peptide antigens suitable for producing antibodies of the invention may be designed, constructed and employed in accordance with well-known techniques. See, e.g., Antibodies: A Laboratory Manual, Chapter 5, p. 75-76, Harlow & Lane Eds., Cold Spring Harbor Laboratory (1988); Czernik, Methods In Enzymology, 201: 264-283 (1991); Merrifield, J. Am. Chem. Soc. 85: 21-49 (1962)). Suitable peptide antigens may comprise all or partial sequence of a trypsin-digested fragment as set forth in Column C of Tables 1 and 2. Suitable peptide antigens may also comprise all or partial sequence of a peptide fragment produced by another protease digestion.

In some embodiments the immunogen is administered with an adjuvant. Suitable adjuvants will be well known to those of skill in the art. Exemplary adjuvants include complete or incomplete Freund's adjuvant, RIBI (muramyl dipeptides) or ISCOM (immunostimulating complexes).

For example, a peptide antigen may be used to produce antibodies that specifically bind the novel Tnk1 site. When the above-described methods are used for producing polyclonal antibodies, following immunization, the polyclonal antibodies which secreted into the bloodstream can be recovered using known techniques. Purified forms of these antibodies can, of course, be readily prepared by standard purification techniques, such as for example, affinity chromatography with Protein A, antiimmunoglobulin, or the antigen itself. In any case, in order to monitor the success of immunization, the antibody levels with respect to the antigen in serum will be monitored using standard techniques such as ELISA, RIA and the like.

Monoclonal antibodies of the invention may be produced by any of a number of means that are well-known in the art. In some embodiments, antibody-producing B cells are isolated from an animal immunized with a peptide antigen as described above. The B cells may be from the spleen, lymph nodes or peripheral blood. Individual B cells are isolated and screened as described below to identify cells producing an antibody specific for the novel site of interest. Identified cells are then cultured to produce a monoclonal antibody of the invention. Alternatively, a monoclonal site-specific antibody of the invention may be produced using standard hybridoma technology, in a hybridoma cell line according to the well-known technique of Kohler and Milstein. See Nature 265: 495-97 (1975); Kohler and Milstein, Eur. J. Immunol. 6: 511 (1976); see also, Current Protocols in Molecular Biology, Ausubel et al. Eds. (1989). Monoclonal antibodies so produced are highly specific, and improve the selectivity and specificity of diagnostic assay methods provided by the invention. For example, a solution containing the appropriate antigen may be injected into a mouse or other species and, after a sufficient time (in keeping with conventional techniques), the animal is sacrificed and spleen cells obtained. The spleen cells are then immortalized by any of a number of standard means.

Methods of immortalizing cells include, but are not limited to, transfecting them with oncogenes, infecting them with an oncogenic virus and cultivating them under conditions that select for immortalized cells, subjecting them to carcinogenic or mutating compounds, fusing them with an immortalized cell, e.g., a myeloma cell, and inactivating a tumor suppressor gene. See, e.g., Harlow and Lane, supra. If fusion with myeloma cell is used, the myeloma cell preferably does not secrete immunoglobulin polypeptides encoded by its own geome (a non-secretory cell line). Typically the antibody producing cell and the immortalized cell (such as but not limited to myeloma cells) with which it is fused are from the same species. Rabbit fusion hybridomas, for example, may be produced as described in U.S. Pat. No. 5,675,063, C. Knight, Issued Oct. 7, 1997. The immortalized antibody producing cells, such as hybridoma cells, are then grown in a suitable selection media, such as hypoxanthine-aminopterin-thymidine (HAT), and the supernatant screened for monoclonal antibodies having the desired specificity, as described below. The secreted antibody may be recovered from tissue culture supernatant by conventional methods such as precipitation, ion exchange or affinity chromatography, or the like.

The invention also encompasses antibody-producing cells and cell lines, such as hybridomas, as described above.

Polyclonal or monoclonal antibodies may also be obtained through in vitro immunization. For example, phage display techniques can be used to provide libraries containing a repertoire of antibodies with varying affinities for a particular antigen. Techniques for the identification of high affinity human antibodies from such libraries are described by Griffiths et al, (1994) EMBO J, 13:3245-3260; Nissim et al, ibid, pp. 692-698 and by Griffiths et al, ibid, 12:725-734, which are incorporated by reference.

The antibodies may be produced recombinantly using methods well known in the art for example, according to the methods disclosed in U.S. Pat. No. 4,349,893 (Reading) or U.S. Pat. No. 4,816,567 (Cabilly et al.) The antibodies may also be chemically constructed by specific antibodies made according to the method disclosed in U.S. Pat. No. 4,676,980 (Segel et al)

Once a desired Tnk1 site-specific antibody is identified, polynucleotides encoding the antibody, such as heavy, light chains or both (or single chains in the case of a single chain antibody) or portions thereof such as those encoding the variable region, may be cloned and isolated from antibody-producing cells using means that are well known in the art. For example, the antigen combining site of the monoclonal antibody can be cloned by PCR and single-chain antibodies produced as phage-displayed recombinant antibodies or soluble antibodies in *E. coli* {see, e.g., Antibody Engineering Protocols, 1995, Humana Press, Sudhir Paul editor.)

Accordingly, in a further aspect, the invention provides such nucleic acids encoding the heavy chain, the light chain, a variable region, a framework region or a CDR of an antibody of the invention. In some embodiments, the nucleic acids are operably linked to expression control sequences. The invention, thus, also provides vectors and expression control sequences useful for the recombinant expression of an antibody or antigen-binding portion thereof of the invention. Those of skill in the art will be able to choose vectors and expression systems that are suitable for the host cell in which the antibody or antigen-binding portion is to be expressed.

Monoclonal antibodies of the invention may be produced recombinantly by expressing the encoding nucleic acids in a suitable host cell under suitable conditions. Accordingly, the invention further provides host cells comprising the nucleic acids and vectors described above.

Monoclonal Fab fragments may also be produced in *E. coli* by known recombinant techniques. See, e.g., W. Huse, Science 246: 1275-81 (1989); Mullinax et al., Proc. Nat.'l Acad ScL 87: 8095 (1990). If monoclonal antibodies of a single isotype are intended for a particular application, particular isotypes can be prepared directly, by selecting from the initial fusion, or prepared secondarily, from a parental hybridoma secreting a monoclonal antibody of different isotype by using the sib selection technique to isolate class-switch variants (Steplewski, et al, Proc. Nat.'l. Acad. ScL, 82: 8653 (1985); Spira et al, J. Immunol. Methods, 74: 307 (1984)). Alternatively, the isotype of a monoclonal antibody with desirable propertied can be changed using antibody engineering techniques that are well-known in the art.

Tnk1 site-specific antibodies of the invention, whether polyclonal or monoclonal, may be screened for epitope and phospho-specificity according to standard techniques. See, e.g., Czernik et al., Methods in Enzymology, 201: 264-283 (1991). For example, the antibodies may be screened against the phosphorylated and/or unphosphorylated peptide library by ELISA to ensure specificity for both the desired antigen (i.e. that epitope including a phosphorylation site of the invention and for reactivity only with the phosphorylated (or unphosphorylated) form of the antigen. Peptide competition assays may be carried out to confirm lack of reactivity with other phospho-epitopes on the parent protein. The antibodies may also be tested by Western blotting against cell preparations containing the parent signaling protein, e.g., cell lines over-expressing the parent protein, to confirm reactivity with the desired phosphorylated epitope/target. Specificity against the desired phosphorylated epitope may also be examined by constructing mutants lacking phosphorylatable residues at positions outside the desired epitope that are known to be phosphorylated, or by mutating the desired phospho-epitope and confirming lack of reactivity. Tnk1 site-specific antibodies of the invention may exhibit some limited cross-reactivity to related epitopes in non-target proteins. This is not unexpected as most antibodies exhibit some degree of cross-reactivity, and anti-peptide antibodies will often cross-react with epitopes having high homology to the immunizing peptide. See, e.g., Czernik, supra. Cross-reactivity with non-target proteins is readily characterized by Western blotting alongside markers of known molecular weight. Amino acid sequences of cross-reacting proteins may be examined to identify phosphorylation sites with flanking sequences that are highly homologous to that of a site of the invention.

In certain cases, polyclonal antisera may exhibit some undesirable general cross-reactivity to phosphotyrosine itself, which may be removed by further purification of antisera, e.g., over a phosphotyramine column. Antibodies of the invention specifically bind their target protein only when phosphorylated (or only when not phosphorylated, as the case may be) at the site, and do not (substantially) bind to the other form (as compared to the form for which the antibody is specific). Antibodies may be further characterized via immunohistochemical (IHC) staining using normal and diseased tissues to examine phosphorylation and activation state and level of a phosphorylation site in diseased tissue. IHC may be carried out according to well-known techniques. See, e.g., Antibodies: A Laboratory Manual, Chapter 10, Harlow & Lane Eds., Cold Spring Harbor Laboratory (1988). Briefly, paraffin-embedded tissue (e.g., tumor tissue) is prepared for immunohistochemical staining by deparaffinizing tissue sections with xylene followed by ethanol; hydrating in water then PBS; unmasking antigen by heating slide in sodium citrate buffer; incubating sections in hydrogen peroxide; blocking in blocking solution; incubating slide in primary antibody and secondary antibody; and finally detecting using ABC avidin/biotin method according to manufacturer's instructions.

Antibodies may be further characterized by flow cytometry carried out according to standard methods. See Chow et al, Cytometry (Communications in Clinical Cytometry) 46: 72-78 (2001). Briefly and by way of example, the following protocol for cytometric analysis may be employed: samples may be centrifuged on Ficoll gradients to remove lysed erythrocytes and cell debris. Adhering cells may be scrapped off plates and washed with PBS. Cells may then be fixed with 2% paraformaldehyde for 10 minutes at 37° C. followed by permeabilization in 90% methanol for 30 minutes on ice. Cells may then be stained with the primary phosphorylation site-specific antibody of the invention (which detects a parent signaling protein enumerated in Table 1), washed and labeled with a fluorescent-labeled secondary antibody. Additional fluorochrome-conjugated marker antibodies (e.g., CD45, CD34) may also be added at this time to aid in the subsequent identification of specific hematopoietic cell types. The cells would then be analyzed on a flow cytometer {e.g. a Beckman Coulter FC500) according to the specific protocols of the instrument used.

Antibodies of the invention may also be advantageously conjugated to fluorescent dyes (e.g. Alexa488, PE) for use in multi-parametric analyses along with other signal transduction (phospho-CrkL, phospho-Erk 1/2) and/or cell marker (CD34) antibodies. Tnk1 site-specific antibodies of the invention may specifically bind to a signaling protein or polypeptide only when phosphorylated at the specified tyrosine residue, but are not limited only to binding to the listed signaling proteins of human species, per se. The invention includes antibodies that also bind conserved and highly homologous or identical phosphorylation sites in respective signaling proteins from other species (e.g., mouse, rat, monkey, yeast), in addition to binding the phosphorylation site of the human homologue. The term "homologous" refers to two or more sequences or subsequences that have at least about 85%, at least 90%, at least 95%, or higher nucleotide or amino acid residue identity, when compared and aligned for maximum correspondence, as measured using sequence comparison method (e.g., BLAST) and/or by visual inspection. Highly homologous or identical sites conserved in other species can readily be identified by standard sequence comparisons (such as BLAST).

Methods for making bispecific antibodies are within the purview of those skilled in the art. Traditionally, the recombinant production of bispecific antibodies is based on the co-expression of two immunoglobulin heavy-chain/light-chain pairs, where the two heavy chains have different specificities (Milstein and Cuello, Nature, 305:537-539 (1983)). Antibody variable domains with the desired binding specificities (antibody-antigen combining sites) can be fused to immunoglobulin constant domain sequences. In certain embodiments, the fusion is with an immunoglobulin heavy-chain constant domain, including at least part of the hinge, CH2, and CH3 regions. DNAs encoding the immunoglobulin heavy-chain fusions and, if desired, the immunoglobulin light chain, are inserted into separate expression vectors, and are co-transfected into a suitable host organism. For further details of illustrative currently known methods for generating bispecific antibodies see, for example, Suresh et al., Methods in Enzymology, 121:210 (1986); WO 96/27011; Brennan et al., Science 229:81 (1985); Shalaby et al., J. Exp. Med. 175:217-225 (1992); Kostelny et al., J. Immunol. 148(5): 1547-1553 (1992); Hollinger et al., Proc. Natl. Acad. Sci. USA 90:6444-6448 (1993); Gruber et al., J. Immunol. 152:5368 (1994); and Tutt et al., J. Immunol. 147:60 (1991). Bispecific antibodies also include cross-linked or heteroconjugate antibodies. Heteroconjugate antibodies may be made using any convenient cross-linking methods. Suitable cross-linking agents are well known in the art, and are disclosed in U.S. Pat. No. 4,676,980, along with a number of cross-linking techniques.

Various techniques for making and isolating bispecific antibody fragments directly from recombinant cell culture have also been described. For example, bispecific antibodies have been produced using leucine zippers. Kostelny et al., J. Immunol., 148(5):1547-1553 (1992). The leucine zipper peptides from the Fos and Jun proteins may be linked to the Fab' portions of two different antibodies by gene fusion. The antibody homodimers may be reduced at the hinge region to form monomers and then re-oxidized to form the antibody heterodimers. This method can also be utilized for the production of antibody homodimers. A strategy for making bispecific antibody fragments by the use of single-chain Fv (scFv) dimers has also been reported. See Gruber et al., J. Immunol., 152:5368 (1994). Alternatively, the antibodies can be "linear antibodies" as described in Zapata et al. Protein Eng. 8(10):1057-1062 (1995). Briefly, these antibodies comprise a pair of tandem Fd segments ($V_H$-$C_H$I-$V_H$-$C_H$I) which form a pair of antigen binding regions. Linear antibodies can be bispecific or monospecific.

To produce the chimeric antibodies, the portions derived from two different species (e.g., human constant region and murine variable or binding region) can be joined together chemically by conventional techniques or can be prepared as single contiguous proteins using genetic engineering techniques. The DNA molecules encoding the proteins of both the light chain and heavy chain portions of the chimeric antibody can be expressed as contiguous proteins. The method of making chimeric antibodies is disclosed in U.S. Pat. No. 5,677,427; U.S. Pat. No. 6,120,767; and U.S. Pat. No. 6,329,508, each of which is incorporated by reference in its entirety.

Fully human antibodies may be produced by a variety of techniques. One example is trioma methodology. The basic approach and an exemplary cell fusion partner, SPAZ-4, for use in this approach have been described by Oestberg et al., Hybridoma 2:361-367 (1983); Oestberg, U.S. Pat. No. 4,634,664; and Engleman et al., U.S. Pat. No. 4,634,666 (each incorporated by reference in its entirety).

Human antibodies can also be produced from non-human transgenic animals having transgenes encoding at least a segment of the human immunoglobulin locus. The production and properties of animals having these properties are described in detail by, see, e.g., Lonberg et al., WO93/12227; U.S. Pat. No. 5,545,806; and Kucherlapati, et al., WO91/10741; U.S. Pat. No. 6,150,584, which are herein incorporated by reference in their entirety.

Various recombinant antibody library technologies may also be utilized to produce fully human antibodies. For example, one approach is to screen a DNA library from human B cells according to the general protocol outlined by Huse et al., Science 246:1275-1281 (1989). The protocol described by Huse is rendered more efficient in combination with phage-display technology. See, e.g., Dower et al., WO 91/17271 and McCafferty et al., WO 92/01047; U.S. Pat. No. 5,969,108, (each of which is incorporated by reference in its entirety).

Eukaryotic ribosome can also be used as means to display a library of antibodies and isolate the binding human antibodies by screening against the target antigen, as described in Coia G, et al., J. Immunol. Methods 1: 254 (1-2):191-7 (2001); Hanes J. et al., Nat. Biotechnol. 18(12):1287-92 (2000); Proc. Natl. Acad. Sci. U.S.A. 95(24):14130-5 (1998); Proc. Natl. Acad. Sci. U.S.A. 94(10):4937-42 (1997), each which is incorporated by reference in its entirety.

The yeast system is also suitable for screening mammalian cell-surface or secreted proteins, such as antibodies. Antibody libraries may be displayed on the surface of yeast cells for the purpose of obtaining the human antibodies against a target antigen. This approach is described by Yeung, et al., Biotechnol. Prog. 18(2):212-20 (2002); Boeder, E. T., et al., Nat. Biotechnol. 15(6):553-7 (1997), each incorporated by reference in its entirety. Alternatively, human antibody libraries may be expressed intracellularly and screened via the yeast two-hybrid system (WO0200729A2, incorporated by reference in its entirety). Recombinant DNA techniques can be used to produce the recombinant Tnk1 site-specific antibodies described herein, as well as the chimeric or humanized Tnk1 site-specific antibodies, or any other genetically-altered antibodies and the fragments or conjugate thereof in any expression systems including both prokaryotic and eukaryotic expression systems, such as bacteria, yeast, insect cells, plant cells, mammalian cells (e.g., NSO cells). Once produced, the whole antibodies, their dimers, individual light and heavy chains, or other immunoglobulin forms of the present application can be purified according to standard procedures of the art, including ammonium sulfate precipitation, affinity columns, column chromatography, gel electrophoresis and the like (see, generally, Scopes, R., Protein Purification (Springer-Verlag, N.Y., 1982)). Once purified, partially or to homogeneity as desired, the polypeptides may then be used therapeutically (including extracorporeally) or in developing and performing assay procedures, immunofluorescent staining, and the like. (See, generally, Immunological Methods, Vols. I and II (Lefkovits and Pernis, eds., Academic Press, NY, 1979 and 1981). 6. Therapeutic Uses Therapies In a further aspect, the invention provides methods and compositions for therapeutic uses of the peptides or proteins comprising a site of the invention, and site-specific antibodies of the invention.

In one embodiment, the invention provides for a method of treating and/or preventing carcinoma and/or leukemia in a subject, wherein the carcinoma and/or leukemia is associated with the phosphorylation state of a phosphorylation site of Tnk1, whether phosphorylated or dephosphorylated, comprising: administering to a subject in need thereof a therapeutically effective amount of a peptide comprising SEQ ID NOs 1, 2, or 3, or fragment thereof and/or an antibody or antigen-binding fragment thereof that specifically bind to SEQ ID NOs 1, 2, or 3. The antibodies may be full-length antibodies, genetically engineered antibodies, antibody fragments, and antibody conjugates of the invention.

The term "subject" refers to a vertebrate, such as for example, a mammal, or a human. Although present application are primarily concerned with the treatment of human subjects, the disclosed methods may also be used for the treatment of other mammalian subjects such as dogs and cats for veterinary purposes.

In one aspect, the disclosure provides a method of treating carcinoma and/or leukemia in which a peptide or an antibody that reduces at least one biological activity of a targeted signaling protein is administered to a subject. For example, the peptide or the antibody administered may disrupt or modulate the interaction of the target signaling protein with its ligand. Alternatively, the peptide or the antibody may interfere with, thereby reducing, the downstream signal transduction of the parent signaling protein. An antibody that specifically binds the novel tyrosine phosphorylation site only when the tyrosine is phosphorylated, and that does not substantially bind to the same sequence when the tyrosine is not phosphorylated, thereby prevents downstream signal transduction triggered by a phosphotyrosine. Alternatively, an antibody that specifically binds the unphosphorylated target phosphorylation site reduces the phosphorylation at that site and thus reduces activation of the protein mediated by phosphorylation of that site. Similarly, an unphosphorylated peptide may compete with an endogenous phosphorylation site for same kinases, thereby preventing or reducing the phosphorylation of the endogenous target protein. Alternatively, a peptide comprising a phosphorylated tyrosine site but lacking the ability to trigger signal transduction may competitively inhibit interaction of the endogenous protein with the same down-stream ligand(s).

The antibodies of the invention may also be used to target cancer cells for effector-mediated cell death. The antibody disclosed herein may be administered as a fusion molecule that includes a site-targeting portion joined to a cytotoxic moiety to directly kill cancer cells. Alternatively, the antibody may directly kill the cancer cells through complement-mediated or antibody-dependent cellular cytotoxicity.

Accordingly in one embodiment, the antibodies of the present disclosure may be used to deliver a variety of cytotoxic compounds. Any cytotoxic compound can be fused to the present antibodies. The fusion can be achieved chemically or genetically (e.g., via expression as a single, fused molecule). The cytotoxic compound can be a biological, such as a polypeptide, or a small molecule. As those skilled in the art will appreciate, for small molecules, chemical fusion is used, while for biological compounds, either chemical or genetic fusion can be used.

Non-limiting examples of cytotoxic compounds include therapeutic drugs, radiotherapeutic agents, ribosome-inactivating proteins (RIPs), chemotherapeutic agents, toxic peptides, toxic proteins, and mixtures thereof. The cytotoxic drugs can be intracellularly acting cytotoxic drugs, such as short-range radiation emitters, including, for example, short-range, high-energy α-emitters. Enzymatically active toxins and fragments thereof, including ribosome-inactivating proteins, are exemplified by saporin, luffin, momordins, ricin, trichosanthin, gelonin, abrin, etc. Procedures for preparing enzymatically active polypeptides of the immunotoxins are described in WO84/03508 and WO85/03508, which are hereby incorporated by reference. Certain cytotoxic moieties are derived from adriamycin, chlorambucil, daunomycin, methotrexate, neocarzinostatin, and platinum, for example.

Exemplary chemotherapeutic agents that may be attached to an antibody or antigen-binding fragment thereof include TAXOL® (paclitaxel), doxorubicin, verapamil, podophyllotoxin, procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide (VPI 6), tamoxifen, transplatinum, 5-fluorouracil, vincristin, vinblastin, or methotrexate. Procedures for conjugating the antibodies with the cytotoxic agents have been previously described and are within the purview of one skilled in the art.

Alternatively, the antibody can be coupled to high energy radiation emitters, for example, a radioisotope, such as $^{131}$I, a γ-emitter, which, when localized at the tumor site, results in a killing of several cell diameters. See, e.g., S. E. Order, "Analysis, Results, and Future Prospective of the Therapeutic Use of Radiolabeled Antibody in Cancer Therapy", Monoclonal Antibodies for Cancer Detection and Therapy, Baldwin et al. (eds.), PP-303-316 (Academic Press 1985), which is hereby incorporated by reference. Other suitable radioisotopes include α-emitters, such as $^{212}$Bi, $^{213}$Bi, and $^{211}$At, and β-emitters, such as $^{186}$Re and $^{90}$Y.

The inventors have discovered that application of antibodies of the present invention can induce senescence of cells expressing aberrant forms of Tnk1. Thus, coadministration therapies where antibodies are adminstered in conjunction with other therapeutic agents is contemplated.

The peptides and antibodies of the invention may be used in combination with other therapies or with other agents. Other agents include but are not limited to polypeptides, small molecules, chemicals, metals, organometallic compounds, inorganic compounds, nucleic acid molecules, oligonucleotides, aptamers, spiegelmers, antisense nucleic acids, locked nucleic acid (LNA) inhibitors, peptide nucleic acid (PNA) inhibitors, immunomodulatory agents, antigen-binding fragments, prodrugs, and peptidomimetic compounds. In certain embodiments, the antibodies and peptides of the invention may be used in combination with cancer therapies known to one of skill in the art. In certain aspects, the present disclosure relates to combination treatments comprising a Tnk1 site-specific antibody described herein and immunomodulatory compounds, vaccines or chemotherapy. Illustrative examples of suitable immunomodulatory agents that may be used in such combination therapies include agents that block negative regulation of T cells or antigen presenting cells (e.g., anti-CTLA4 antibodies, anti-PD-L1 antibodies, anti-PDL-2 antibodies, anti-PD-1 antibodies and the like) or agents that enhance positive co-stimulation of T cells (e.g., anti-CD40 antibodies or anti 4-IBB antibodies) or agents that increase NK cell number or T-cell activity (e.g., inhibitors such as IMiDs, thalidomide, or thalidomide analogs). Furthermore, immunomodulatory therapy could include cancer vaccines such as dendritic cells loaded with tumor cells, proteins, peptides, RNA, or DNA derived from such cells, patient derived heat-shock proteins (hsp's) or general adjuvants stimulating the immune system at various levels such as CpG, Luivac®, Biostim®, Ribomunyl®, Imudon®, Broncho Vaxom® or any other compound or other adjuvant activating receptors of the innate immune system (e.g., toll like receptor agonist, anti-CTLA-4 antibodies, etc.). Also, immunomodulatory therapy could include treatment with cytokines such as IL-2, GM-CSF and IFN-gamma.

Pharmaceutical compounds that may be used for combinatory anti-tumor therapy include, merely to illustrate: aminoglutethimide, amsacrine, anastrozole, asparaginase, beg, bicalutamide, bleomycin, buserelin, busulfan, camptothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine.

These chemotherapeutic anti-tumor compounds may be categorized by their mechanism of action into groups, including, for example, the following classes of agents: anti-metabolites/anti-cancer agents, such as pyrimidine analogs (5-fluorouracil, floxuridine, capecitabine, gemcitabine and cytarabine) and purine analogs, folate inhibitors and related inhibitors (mercaptopurine, thioguanine, pentostatin and 2-chlorodeoxy adenosine (cladribine)); antiproliferative/antimitotic agents including natural products such as vinca alkaloids (vinblastine, vincristine, and vinorelbine), microtubule disruptors such as taxane (paclitaxel, docetaxel), vincristine, vinblastine, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, Cytoxan, dactinomycin, daunorubicin, doxorubicin, epirubicin, hexamethylmelamineoxaliplatin, iphosphamide, melphalan, mechlorethamine, mitomycin, mitoxantrone, nitrosourea, plicamycin, procarbazine, TAXOL® (paclitaxel), taxotere, teniposide, triethylenethiophosphoramide and etoposide (VPI 6)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); immunomodulatory agents (thalidomide and analogs thereof such as lenalidomide (REVLIMID®, CC-5013) and CC-4047 (Actimid)), cyclophosphamide; anti-angiogenic compounds (TNP-470, genistein) and growth factor inhibitors (vascular endothelial growth factor (VEGF) inhibitors, fibroblast growth factor (FGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin and mitoxantrone, topotecan, irinotecan), corticosteroids (cortisone, dexamethasone, hydrocortisone, methylprednisolone, prednisone, and prenisolone); growth factor signal transduction kinase inhibitors; mitochondrial dysfunction inducers and caspase activators; and chromatin disruptors.

In certain embodiments, pharmaceutical compounds that may be used for combinatory anti-angiogenesis therapy include: (1) inhibitors of release of "angiogenic molecules," such as bFGF (basic fibroblast growth factor); (2) neutralizers of angiogenic molecules, such as anti-βbFGF antibodies; and (3) inhibitors of endothelial cell response to angiogenic stimuli, including collagenase inhibitor, basement membrane turnover inhibitors, angiostatic steroids, fungal-derived angiogenesis inhibitors, platelet factor 4, thrombospondin, arthritis drugs such as D-penicillamine and gold thiomalate, vitamin $D_3$ analogs, alpha-interferon, and the like. For additional proposed inhibitors of angiogenesis, see Blood et al., Biochim Biophys. Acta, 1032:89-118 (1990), Moses et al., Science, 248:1408-1410 (1990), Ingber et al., Lab. Invest., 59:44-51 (1988), and U.S. Pat. Nos. 5,092,885, 5,112,946, 5,192,744, 5,202,352, and 6,573,256. In addition, there are a wide variety of compounds that can be used to inhibit angiogenesis, for example, peptides or agents that block the VEGF-mediated angiogenesis pathway, endostatin protein or derivatives, lysine binding fragments of angiostatin, melanin or melanin-promoting compounds, plasminogen fragments (e.g., Kringles 1-3 of plasminogen), troponin subunits, inhibitors of vitronectin $\alpha_v\beta_3$, peptides derived from Saposin B, antibiotics or analogs (e.g., tetracycline or neomycin), dienogest-containing compositions, compounds comprising a MetAP-2 inhibitory core coupled to a peptide, the compound EM-138, chalcone and its analogs, and naaladase inhibitors. See, for example, U.S. Pat. Nos. 6,395,718, 6,462,075, 6,465,431, 6,475,784, 6,482,802, 6,482,810, 6,500,431, 6,500,924, 6,518,298, 6,521,439, 6,525,019, 6,538,103, 6,544,758, 6,544,947, 6,548,477, 6,559,126, and 6,569,845. 7. Diagnostic Uses Diagnostic and Immunoassay Related Uses In a further aspect, the invention provides methods for detecting and quantitating phosphoyrlation, truncation or mutation of endogenous Tnk1. For example, peptides of the invention, and antibodies of the invention are useful in diagnostic and prognostic evaluation of carcinoma and/or leukemias, wherein the carcinoma and/or leukemia is associated with the phosphorylation state of a phosphorylation site whether phosphorylated or dephosphorylated, or are truncated, or mutated. Methods of diagnosis can be performed in vitro using a biological sample (e.g., blood sample, lymph node biopsy or tissue) from a subject, or in vivo. The phosphorylation state or level at the tyrosine residue identified or presence of truncated or mutated form of Tnk1 may be assessed. A change in the phosphorylation state or level at the phosphorylation site, or truncation or mutation, as compared to a control, indicates that the subject is suffering from, or susceptible to, carcinoma and/or leukemia.

In another embodiment, the phosphorylation state or level at a phosphorylation site is determined by an antibody or antigen-binding fragment thereof, wherein the antibody specifically binds the phosphorylation site. The antibody may be one that only binds to the phosphorylation site when the tyrosine residue is phosphorylated, but does not bind to the same sequence when the tyrosine is not phosphorylated; or vice versa.

Alternatively, the presence of a truncated form of Tnk1 can be detected by a combination assay of comparing binding of an antibody specific for the n-terminus site of Tnk1 versus binding of an antibody specific to a c-terminus site of Tnk1. The absence of signal from the c-terminus specific antibody is indication of the presence of a truncated protein.

In particular embodiments, the antibodies of the present application are attached to labeling moieties, such as a detectable marker. One or more detectable labels can be attached to the antibodies. Exemplary labeling moieties include radiopaque dyes, radiocontrast agents, fluorescent molecules, spin-labeled molecules, enzymes, or other labeling moieties of diagnostic value, particularly in radiologic or magnetic resonance imaging techniques.

A radiolabeled antibody in accordance with this disclosure can be used for in vitro diagnostic tests. The specific activity of an antibody, binding portion thereof, probe, or ligand, depends upon the half-life, the isotopic purity of the radioactive label, and how the label is incorporated into the biological agent. In immunoassay tests generally, the higher the specific activity, the better the sensitivity. Radioisotopes useful as labels, e.g., in diagnostics, include iodine ($^{131}$I or $^{125}$I), indium ($^{111}$In) technetium ($^{99}$Tc), phosphorus ($^{32}$P), carbon ($^{14}$C), sulfur (35S), and tritium ($^{3}$H), or one of the therapeutic isotopes listed above.

Fluorophore and chromophore labeled biological agents can be prepared from standard moieties known in the art. Since antibodies and other proteins absorb light having wavelengths up to about 310 nm, the fluorescent moieties may be selected to have substantial absorption at wavelengths above 310 nm, such as for example, above 400 nm. A variety of suitable fluorescers and chromophores are described by Stryer, Science, 162:526 (1968) and Brand et al., Annual Review of Biochemistry, 41:843-868 (1972), which are hereby incorporated by reference. The antibodies can be labeled with fluorescent chromophore groups by conventional procedures such as those disclosed in U.S. Pat. Nos. 3,940,475, 4,289,747, and 4,376,110, which are hereby incorporated by reference.

The control may be parallel samples providing a basis for comparison, for example, biological samples drawn from a healthy subject, or biological samples drawn from healthy tissues of the same subject. Alternatively, the control may be a pre-determined reference or threshold amount. If the subject is being treated with a therapeutic agent, and the progress of the treatment is monitored by detecting the tyrosine phosphorylation state level at a phosphorylation site of the invention, a control may be derived from biological samples drawn from the subject prior to, or during the course of the treatment.

In certain embodiments, antibody conjugates for diagnostic use in the present application are intended for use in vitro, where the antibody is linked to a secondary binding ligand or to an enzyme (an enzyme tag) that will generate a colored product upon contact with a chromogenic substrate. Examples of suitable enzymes include urease, alkaline phosphatase, (horseradish) hydrogen peroxidase and glucose oxidase. In certain embodiments, secondary binding ligands are biotin and avidin or streptavidin compounds.

Immunoassay formats and variations thereof, which may be useful for carrying out the methods disclosed herein, are well known in the art. See generally E. Maggio, Enzyme-Immunoassay, (1980) (CRC Press, Inc., Boca Raton, Fla.); see also, e.g., U.S. Pat. No. 4,727,022 (Skold et al, "Methods for Modulating Ligand-Receptor Interactions and their Application"); U.S. Pat. No. 4,659,678 (Forrest et al, "Immunoassay of Antigens"); U.S. Pat. No. 4,376,110 (David et al, "Immunometric Assays Using Monoclonal Antibodies"). Conditions suitable for the formation of reagent-antibody complexes are well known to those of skill in the art. See id. The TNK1-specific antibodies described herein may be used in a "two-site" or "sandwich" assay, with a single hybridoma cell line serving as a source for both the labeled monoclonal antibody and the bound monoclonal antibody. Such assays are described in U.S. Pat. No. 4,376,110. The concentration of detectable reagent should be sufficient such that the binding of the antibody's target molecule (e.g., a TNK1 phosphorylated Y277 residue) is detectable compared to background.

Antibodies useful in the practice of the methods disclosed herein may be conjugated to a solid support suitable for a diagnostic assay (e.g., beads, plates, slides or wells formed from materials such as latex or polystyrene) in accordance with known techniques, such as precipitation. Antibodies or other binding reagents may likewise be conjugated to detectable groups such as radiolabels (e.g., $^{35}S$, $^{125}I$, $^{131}I$), enzyme labels (e.g., horseradish peroxidase, alkaline phosphatase), and fluorescent labels (e.g., fluorescein) in accordance with known techniques.

Cell-based assays, such flow cytometry (FC), immuno-histochemistry (IHC), or immunofluorescence (IF) are particularly desirable in practicing the methods of the invention, since such assay formats are clinically-suitable, allow the detection of mutant TNK1 kinase polypeptide expression in vivo, and avoid the risk of artifact changes in activity resulting from manipulating cells obtained from, e.g. a tumor sample in order to obtain extracts. Accordingly, in some embodiments, the methods of the invention are implemented in a flow-cytometry (FC), immuno-histochemistry (IHC), or immunofluorescence (IF) assay format.

Flow cytometry (FC) may be employed to determine the expression of mutant TNK1 kinase polypeptide in a mammalian tumor before, during, and after treatment with a drug targeted at inhibiting TNK1 kinase activity. For example, tumor cells from a bone marrow sample may be analyzed by flow cytometry for TNK1-C17ORF61 fusion polypeptide expression and/or activation, as well as for markers identifying cancer cell types, etc., if so desired. Flow cytometry may be carried out according to standard methods. See, e.g. Chow et al, Cytometry (Communications in Clinical Cytometry) 46: 72-78 (2001). Briefly and by way of example, the following protocol for cytometric analysis may be employed: fixation of the cells with 2% paraformaldehyde for 10 minutes at 37° C. followed by permeabilization in 90% methanol for 30 minutes on ice. Cells may then be stained with the primary phospho-Tnk1 (e.g., Y77, 277, or 287)-specific antibody, washed and labeled with a fluorescent-labeled secondary antibody. The cells would then be analyzed on a flow cytometer (e.g. a Beckman Coulter FC500) according to the specific protocols of the instrument used. Such an analysis would identify the level of expressed or phospho-Tnk1 (Y77, 277, or 287) in the tumor. Similar analysis after treatment of the tumor with a Tnk1-inhibiting therapeutic would reveal the responsiveness of a phospho-TNK1 polypeptide-expressing tumor to the targeted inhibitor of TNK1 kinase. Immunohistochemical (IHC) staining may be also employed to determine the expression and/or activation status of mutant TNK1 kinase polypeptide in a mammalian cancer (e.g. HL) before, during, and after treatment with a drug targeted at inhibiting TNK1 kinase activity. IHC may be carried out according to well-known techniques. See, e.g., ANTIBODIES: A LABORATORY MANUAL, Chapter 10, Harlow & Lane Eds., Cold Spring Harbor Laboratory (1988).

Briefly, and by way of example, paraffin-embedded tissue (e.g. tumor tissue from a biopsy) is prepared for immunohistochemical staining by deparaffinizing tissue sections with xylene followed by ethanol; hydrating in water then PBS; unmasking antigen by heating slide in sodium citrate buffer; incubating sections in hydrogen peroxide; blocking in blocking solution; incubating slide in primary phospho-Tnk1 (e.g., Y77, Y235, Y277, Y287, or Y353) antibody, and secondary antibody; and finally detecting using a detectable label on the secondary antibody (e.g., an streptavidin-labeled secondary detected with a biotin-substrate).

Immunofluorescence (IF) assays may be also employed to determine the expression and/or activation status of an aberrantly expressed TNK1 polypeptide in a mammalian cancer before, during, and after treatment with a drug targeted at inhibiting TNK1 kinase activity. IF may be carried out according to well-known techniques. See, e.g., J. M. Polak and S. Van Noorden (1997) INTRODUCTION TO IMMUNOCYTOCHEMISTRY, 2nd Ed.; ROYAL MICROSCOPY SOCIETY MICROSCOPY HANDBOOK 37, BioScientific/Springer-Verlag. Briefly, and by way of example, patient samples may be fixed in paraformaldehyde followed by methanol, blocked with a blocking solution such as horse serum, incubated with the primary antibody followed by a secondary antibody labeled with a fluorescent dye such as Alexa 488 and analyzed with an epifluorescent microscope. Antibodies employed in the above-described assays may be advantageously conjugated to fluorescent dyes (e.g. Alexa488, PE), or other labels, such as quantum dots, for use in multi-parametric analyses along with other signal transduction (EGFR, phospho-AKT, phospho-Erk 1/2) and/or cell marker (cytokeratin) antibodies.

A variety of other protocols, including enzyme-linked immunosorbent assay (ELISA), radio-immunoassay (RIA), and fluorescent-activated cell sorting (FACS), for measuring aberrantly expressed TNK1 are known in the art and provide a basis for diagnosing the presence of aberrantly expressed TNK1. Normal or standard values for expression of wild-type TNK1 expression are established by combining body fluids or cell extracts taken from normal (e.g., non-cancerous) mammalian subjects, such as human subjects, with one of the phosphoTNK-specific antibodies described herein to under conditions suitable for complex formation. The amount of standard complex formation may be quantified by various methods (e.g., by photometric means). Quantities of phosphorylated and/or truncated TNK1 expressed in subject, control, and disease samples from biopsied tissues are compared with the standard values. Deviation between standard and subject values establishes the parameters for diagnosing disease.

Antibodies of the invention may also be optimized for use in an immuno assay to determine the activation/phosphorylation status of a target signaling protein in subjects before, during, and after treatment with a therapeutic agent targeted at inhibiting tyrosine phosphorylation at the phosphorylation site disclosed herein. For example, bone marrow cells or peripheral blood cells from patients may be analyzed by flow cytometry for target signaling protein phosphorylation, as well as for markers identifying various hematopoietic cell types. In this manner, activation status of the malignant cells may be specifically characterized. Flow cytometry may be carried out according to standard methods. See, e.g., Chow et al, Cytometry (Communications in Clinical Cytometry) 46: 72-78 (2001).

Alternatively, antibodies of the invention may be used in immunohistochemical (IHC) staining to detect differences in signal transduction or protein activity using normal and diseased tissues. IHC may be carried out according to well-known techniques. See, e.g., Antibodies: A Laboratory Manual, supra.

In another aspect, the invention provides a method for identifying an agent that modulates tyrosine phosphorylation at a site of the invention, comprising: a) contacting a candidate agent with a peptide or protein comprising a phosphorylation site of the invention; and b) determining the phosphorylation state or level at the novel phosphorylation site. A change in the phosphorylation level of the specified tyrosine in the presence of the test agent, as compared to a control, indicates that the candidate agent potentially modulates tyrosine phosphorylation at a novel phosphorylation site of the invention.

In another embodiment, the phosphorylation state or level at a phosphorylation site is determined by an antibody or antigen-binding fragment thereof, wherein the antibody specifically binds the phosphorylation site. The antibody may be one that only binds to the phosphorylation site when the tyrosine residue is phosphorylated, but does not bind to the same sequence when the tyrosine is not phosphorylated; or vice versa.

In particular embodiments, the antibodies of the present application are attached to labeling moieties, such as a detectable marker. The control may be parallel samples providing a basis for comparison, for example, the phosphorylation level of the target protein or peptide in absence of the testing agent. Alternatively, the control may be a pre-determined reference or threshold amount.

In another aspect, the present application concerns immunoassays for binding, purifying, quantifying and otherwise generally detecting the phosphorylation state or level at a phosphorylation site of the invention, or presence of truncated form of Tnk1.

Assays may be homogeneous assays or heterogeneous assays. In a homogeneous assay the immunological reaction usually involves a phosphorylation site-specific antibody of the invention, a labeled analyte, and the sample of interest. The signal arising from the label is modified, directly or indirectly, upon the binding of the antibody to the labeled analyte. Both the immunological reaction and detection of the extent thereof are carried out in a homogeneous solution. Immunochemical labels that may be used include free radicals, radioisotopes, fluorescent dyes, enzymes, bacteriophages, coenzymes, and so forth.

In a heterogeneous assay approach, the reagents are usually the specimen, a site-specific antibody of the invention, and suitable means for producing a detectable signal. Similar specimens as described above may be used. The antibody is generally immobilized on a support, such as a bead, plate or slide, and contacted with the specimen suspected of containing the antigen in a liquid phase. The support is then separated from the liquid phase and either the support phase or the liquid phase is examined for a detectable signal using means for producing such signal. The signal is related to the presence of the analyte in the specimen. Means for producing a detectable signal include the use of radioactive labels, fluorescent labels, enzyme labels, and so forth.

Site-specific antibodies disclosed herein may be conjugated to a solid support suitable for a diagnostic assay (e.g., beads, plates, slides or wells formed from materials such as latex or polystyrene) in accordance with known techniques, such as precipitation. In certain embodiments, immunoassays are the various types of enzyme linked immunoadsorbent assays (ELISAs) and radioimmunoassays (RIA) known in the art Immunohistochemical (IHC) detection using tissue sections is also particularly useful, as are immuno-fluorescence (IF) methods. However, it will be readily appreciated that detection is not limited to such techniques, and Western blotting, dot and slot blotting, FACS analyses, and the like may also be used. The steps of various useful immunoassays have been described in the scientific literature, such as, e.g., Nakamura et al., in Enzyme Immunoassays: Heterogeneous and Homogeneous Systems, Chapter 27 (1987), incorporated herein by reference.

In general, the detection of immunocomplex formation is well known in the art and may be achieved through the application of numerous approaches. These methods are based upon the detection of radioactive, fluorescent, biological or enzymatic tags. Of course, one may find additional advantages through the use of a secondary binding ligand such as a second antibody or a biotin/avidin ligand binding arrangement, as is known in the art. The antibody used in the detection may itself be conjugated to a detectable label, wherein one would then simply detect this label. The amount of the primary immune complexes in the composition would, thereby, be determined.

Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under conditions effective and for a period of time sufficient to allow the formation of secondary immune complexes. The secondary immune complexes are washed extensively to remove any non-specifically bound labeled secondary antibodies or ligands, and the remaining label in the secondary immune complex is detected. An enzyme linked immunoadsorbent assay (ELISA) is a type of binding assay. In one type of ELISA, site-specific antibodies disclosed herein are immobilized onto a selected surface exhibiting protein affinity (e.g., a well in a polystyrene micro titer plate). Then, a suspected neoplastic tissue sample is added to the wells. After binding and washing to remove non-specifically bound immune complexes, the bound target signaling protein may be detected. In another type of ELISA, the neoplastic tissue samples are immobilized onto the well surface and then contacted with the site-specific antibodies disclosed herein. After binding and washing to remove non-specifically bound immune complexes, the bound site-specific antibodies are detected. Irrespective of the format used, ELISAs have certain features in common, such as coating, incubating or binding, washing to remove non-specifically bound species, and detecting the bound immune complexes.

The radioimmunoassay (RIA) is an analytical technique which depends on the competition (affinity) of an antigen for antigen-binding sites on antibody molecules. Standard curves are constructed from data gathered from a series of samples each containing the same known concentration of labeled antigen, and various, but known, concentrations of unlabeled antigen. Antigens are labeled with a radioactive isotope tracer. The mixture is incubated in contact with an antibody. Then the free antigen is separated from the antibody and the antigen bound thereto. Then, by use of a suitable detector, such as a gamma or beta radiation detector, the percent of either the bound or free labeled antigen or both is determined. This procedure is repeated for a number of samples containing various known concentrations of unlabeled antigens and the results are plotted as a standard graph. The percent of bound tracer antigens is plotted as a function of the antigen concentration. Typically, as the total antigen concentration increases the relative amount of the tracer antigen bound to the antibody decreases. After the standard graph is prepared, it is thereafter used to determine the concentration of antigen in samples undergoing analysis.

In an analysis, the sample in which the concentration of antigen is to be determined is mixed with a known amount of tracer antigen. Tracer antigen is the same antigen known to be in the sample but which has been labeled with a suitable radioactive isotope. The sample with tracer is then incubated in contact with the antibody. Then it can be counted in a suitable detector which counts the free antigen remaining in the sample. The antigen bound to the antibody or immunoadsorbent may also be similarly counted. Then, from the standard curve, the concentration of antigen in the original sample is determined.

Formulations and Modes of Administration

Methods of administration of therapeutic agents, particularly peptide and antibody therapeutics, are well-known to those of skill in the art.

Peptides of the invention can be administered in the same manner as conventional peptide type pharmaceuticals. In some embodiments, peptides are administered parenterally, for example, intravenously, intramuscularly, intraperitoneally, or subcutaneously. When administered orally, peptides may be proteolytically hydrolyzed. Therefore, oral application may not be usually effective. However, peptides can be administered orally as a formulation wherein peptides are not easily hydrolyzed in a digestive tract, such as liposome-microcapsules. Peptides may be also administered in suppositories, sublingual tablets, or intranasal spray.

If administered parenterally, one pharmaceutical composition is an aqueous solution that, in addition to a peptide of the invention as an active ingredient, may contain for example, buffers such as phosphate, acetate, etc., osmotic pressure-adjusting agents such as sodium chloride, sucrose, and sorbitol, etc., antioxidative or antioxygenic agents, such as ascorbic acid or tocopherol and preservatives, such as antibiotics. The parenterally administered composition also may be a solution readily usable or in a lyophilized form which is dissolved in sterile water before administration.

The pharmaceutical formulations, dosage forms, and uses described below generally apply to antibody-based therapeutic agents, but are also useful and can be modified, where necessary, for making and using therapeutic agents of the disclosure that are not antibodies. To achieve the desired therapeutic effect, the site-specific antibodies or antigen-binding fragments thereof can be administered in a variety of unit dosage forms. The dose will vary according to the particular antibody. For example, different antibodies may have different masses and/or affinities, and thus require different dosage levels. Antibodies prepared as Fab or other fragments will also require differing dosages than the equivalent intact immunoglobulins, as they are of considerably smaller mass than intact immunoglobulins, and thus require lower dosages to reach the same molar levels in the patient's blood. The dose will also vary depending on the manner of administration, the particular symptoms of the patient being treated, the overall health, condition, size, and age of the patient, and the judgment of the prescribing physician. Dosage levels of the antibodies for human subjects are generally between about 1 mg per kg and about 100 mg per kg per patient per treatment, such as for example, between about 5 mg per kg and about 50 mg per kg per patient per treatment. In terms of plasma concentrations, the antibody concentrations may be in the range from about 25 μg/mL to about 500 μg/mL. However, greater amounts may be required for extreme cases and smaller amounts may be sufficient for milder cases.

Administration of an antibody will generally be performed by a parenteral route, typically via injection such as intra-articular or intravascular injection (e.g., intravenous infusion) or intramuscular injection. Other routes of administration, e.g., oral (p.o.), may be used if desired and practicable for the particular antibody to be administered. An antibody can also be administered in a variety of unit dosage forms and their dosages will also vary with the size, potency, and in vivo half-life of the particular antibody being administered. Doses of a site-specific antibody will also vary depending on the manner of administration, the particular symptoms of the patient being treated, the overall health, condition, size, and age of the patient, and the judgment of the prescribing physician.

The frequency of administration may also be adjusted according to various parameters. These include the clinical response, the plasma half-life of the antibody, and the levels of the antibody in a body fluid, such as, blood, plasma, serum, or synovial fluid. To guide adjustment of the frequency of administration, levels of the antibody in the body fluid may be monitored during the course of treatment.

Formulations particularly useful for antibody-based therapeutic agents are also described in U.S. Patent App. Publication Nos. 20030202972, 20040091490 and 20050158316. In certain embodiments, the liquid formulations of the application are substantially free of surfactant and/or inorganic salts. In another specific embodiment, the liquid formulations have a pH ranging from about 5.0 to about 7.0. In yet another specific embodiment, the liquid formulations comprise histidine at a concentration ranging from about 1 mM to about 100 mM. In still another specific embodiment, the liquid formulations comprise histidine at a concentration ranging from 1 mM to 100 mM. It is also contemplated that the liquid formulations may further comprise one or more excipients such as a saccharide, an amino acid (e.g., arginine, lysine, and methionine) and a polyol. Additional descriptions and methods of preparing and analyzing liquid formulations can be found, for example, in PCT publications WO 03/106644, WO 04/066957, and WO 04/091658.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the pharmaceutical compositions of the application.

In certain embodiments, formulations of the subject antibodies are pyrogen-free formulations which are substantially free of endotoxins and/or related pyrogenic substances. Endotoxins include toxins that are confined inside microorganisms and are released when the microorganisms are broken down or die. Pyrogenic substances also include fever-inducing, thermostable substances (glycoproteins) from the outer membrane of bacteria and other microorganisms. Both of these substances can cause fever, hypotension and shock if administered to humans. Due to the potential harmful effects, it is advantageous to remove even low amounts of endotoxins from intravenously administered pharmaceutical drug solutions. The Food & Drug Administration ("FDA") has set an upper limit of 5 endotoxin units (EU) per dose per kilogram body weight in a single one hour period for intravenous drug applications (The United States Pharmacopeial Convention, Pharmacopeial Forum 26 (1): 223 (2000)). When therapeutic proteins are administered in amounts of several hundred or thousand milligrams per kilogram body weight, as can be the case with monoclonal antibodies, it is advantageous to remove even trace amounts of endotoxin.

The amount of the formulation which will be therapeutically effective can be determined by standard clinical techniques. In addition, in vitro assays may optionally be used to help identify optimal dosage ranges. The precise dose to be used in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems. The dosage of the compositions to be administered can be determined by the skilled artisan without undue experimentation in conjunction with standard dose-response studies. Relevant circumstances to be considered in making those determinations include the condition or conditions to be treated, the choice of composition to be administered, the age, weight, and response of the individual patient, and the severity of the patient's symptoms. For example, the actual patient body weight may be used to calculate the dose of the formulations in milliliters (mL) to be administered. There may be no downward adjustment to "ideal" weight. In such a situation, an appropriate dose may be calculated by the following formula: Dose (mL)=[patient weight (kg)×dose level (mg/kg)/drug concentration (mg/mL)] For the purpose of treatment of disease, the appropriate dosage of the compounds (for example, antibodies) will depend on the severity and course of disease, the patient's clinical history and response, the toxicity of the antibodies, and the discretion of the attending physician. The initial candidate dosage may be administered to a patient. The proper dosage and treatment regimen can be established by monitoring the progress of therapy using conventional techniques known to those of skill in the art.

The formulations of the application can be distributed as articles of manufacture comprising packaging material and a pharmaceutical agent which comprises, e.g., the antibody and a pharmaceutically acceptable carrier as appropriate to the mode of administration. The packaging material will include a label which indicates that the formulation is for use in the treatment of cancer.

Kits

Antibodies and peptides of the invention may also be used within a kit for detecting the phosphorylation state or level at a phosphorylation site of the invention or truncation or mutation of Tnk1, comprising at least one of the following: a peptide of SEQ ID NOs. 1, 2, and/or 3, or an antibody or an antigen-binding fragment thereof; and a Tnk1 site specific antibody containing composition. Such a kit may further comprise a packaged combination of reagents in predetermined amounts with instructions for performing the diagnostic assay. Where the antibody is labeled with an enzyme, the kit will include substrates and co-factors required by the enzyme. In addition, other additives may be included such as stabilizers, buffers and the like. The relative amounts of the various reagents may be varied widely to provide for concentrations in solution of the reagents that substantially optimize the sensitivity of the assay. Particularly, the reagents may be provided as dry powders, usually lyophilized, including excipients that, on dissolution, will provide a reagent solution having the appropriate concentration.

The teachings of the references cited throughout the specification are incorporated herein in their entirety by this reference to the extent they are not inconsistent with the teachings herein. It should be understood that the examples and the embodiments described herein are for illustrative purposes only and that various modifications or changes in light thereof will be suggested to persons skilled in the art and are to be included within the spirit and purview of this application.

Examples

The inventors have recently identified three Tnk1 substrates Grb2, STAT1 and Cdk1. All 3 proteins are known suppressors of cell growth when tyrosine (Y) phosphorylated (1, 4, 7). For example, phosphorylation of Grb2 by Tnk1 results in the dissociation of the Grb2-Sos1 Ras GEF complex that cause inhibition/loss of Ras activity and suppression of the Ras-Raf1-Mapk cell growth pathway (1, 4, 5). Similarly, Y-phosphorylation of STAT1 by Tnk1 results in the activation of STAT1, which is a well known DNA damage sensor (FIG. 1; 7, Hoare et al Unpublished data).

Exogenous stimulus by TNFα is known to activate STAT1 through other protein tyrosine kinases such as the Jaks (6). However, the data presented herein indicates that Tnk1, but not the inactive Tnk1 that has lost its protein tyrosine kinase (PTK) activity, can activate STAT1 in the absence of exogenous stimulation. Since Tnk1's tumor suppressor function depends on its PTK activity, it is found that functional loss of Tnk1 in knockout mice and in human cancer cell lines results in a concomitant loss $Y^{701}$ phosphorylation of STAT1 allowing STAT1 to remain in its inactive state in the cells (FIG. 2; Hoare et. al. unpublished data).

Tumor growth and metastasis occurs when STAT1 is inactive and hence activated STAT1 is known to be the gatekeeper or the first line of defense against cancer or infection that may result in cancer (7). It has been found that loss of Tnk1 function can occur in human and mice through mutations (SNPs; 1, 8, Hoare et. al. unpublished data), deletion (9) or epigenetic silencing (1, 4, Hoare et. al. unpublished data). Since Tnk1 is upstream of STAT1, functional loss of Tnk1 must have to occur first, which may account for the inactivation of STAT1 in human tumor cell lines. Hence, activation of inactive Tnk1 is an ideal therapeutic strategy for cancer.

Figure 2:
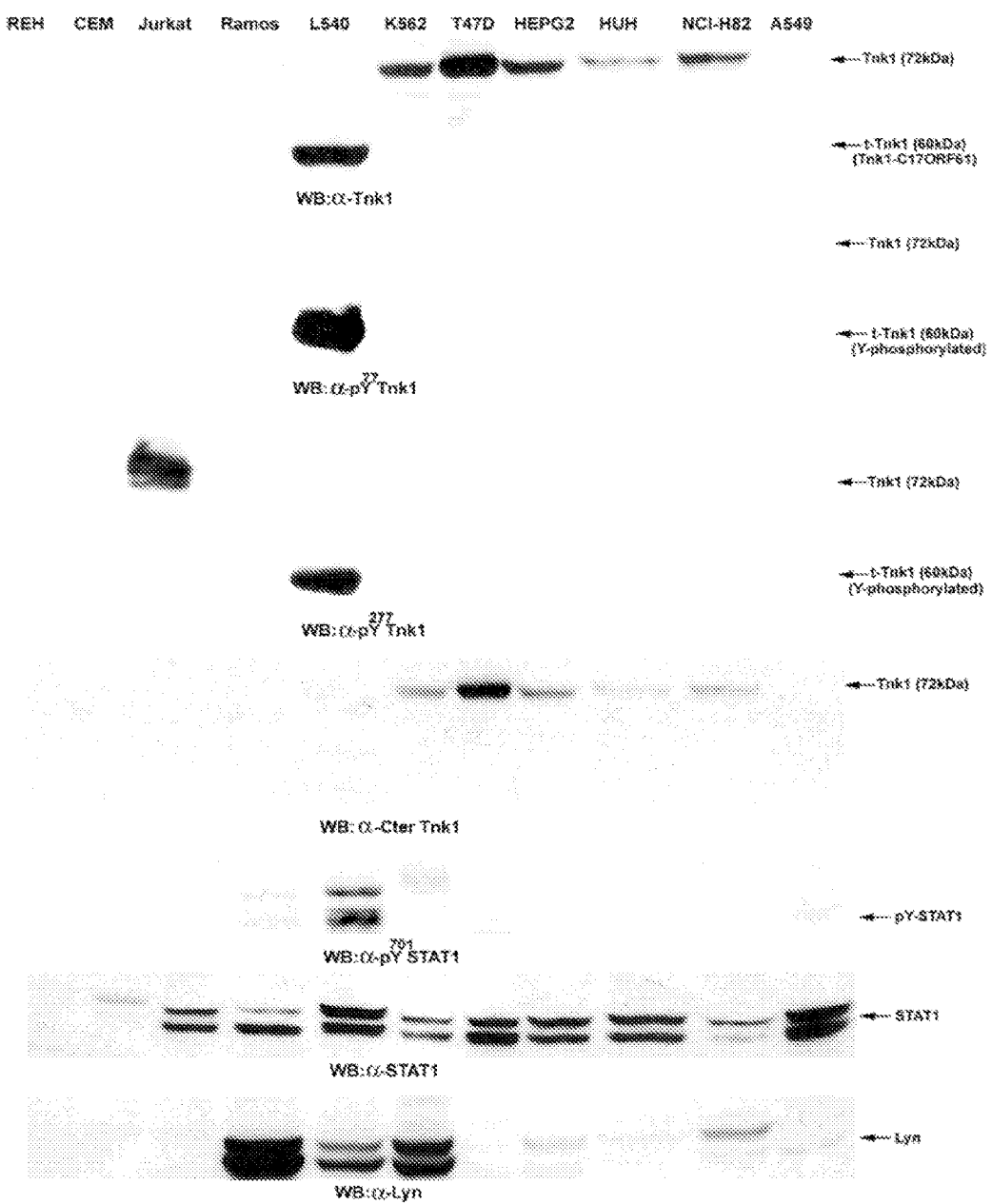
FIG. 2: Expression of Tnk1 in human cell lines. Tnk1 is not expressed in REH (a nonB/nonT-cell), CEM, Jurkat (T-cell), Ramos (B-Cell) and A547 (Non Small Cell Lung Cancer) lines by Western analysis of cell lysate (100 μg protein). The cell lines L540 (B-cell), K562 (Myeloid leukemia), T47D (breast), HEPG2, HUH (liver) and NC1-H82 (Small Cell Lung Cancer) express Tnk1. With the exception of L540, the expressed 72 kDa Tnk1 is not phosphorylated at Y77 or Y277. The L540 cells express a 60 kDa truncated Tnk-(C17Orf61) fusion protein (tTnk1) phosphorylated at both Y77 and Y277. The anti C-terminal Tnk1 (B) antibody fails to detect t-Tnk1. STAT1 remains inactive in the cells that express inactive Tnk1 or tTnk1 while STAT3 is found to be Y-phosphorylated and activated in the absence or presence of Tnk1 or t-Tnk1 respectively.
Figure 3:
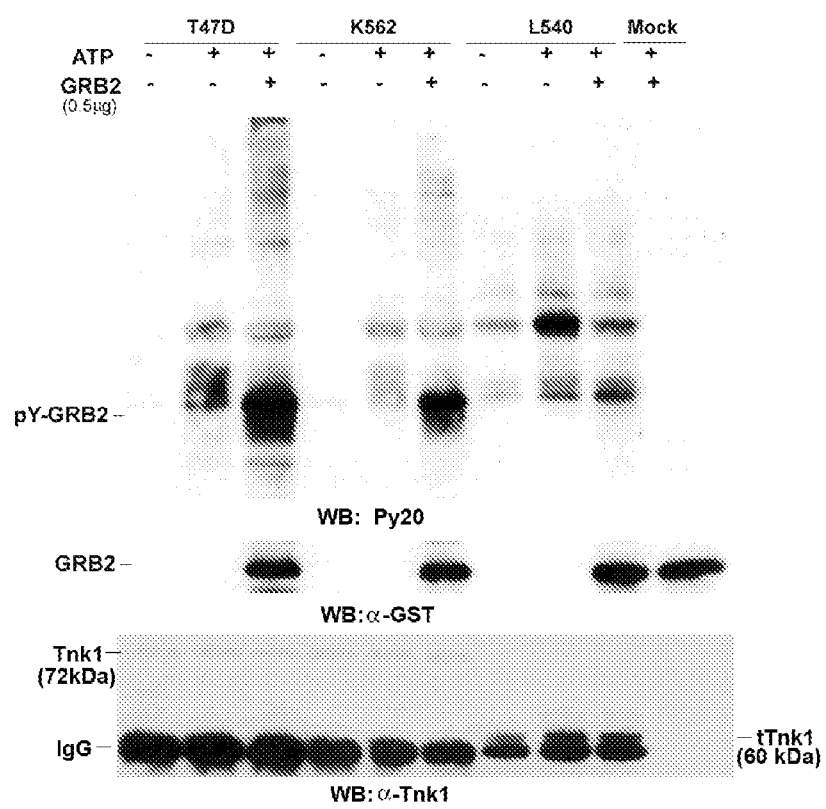
FIG. 3: In Vitro Tnk1 Kinase Assay Using Grb2, substrate. The 72 kDa Tnk1 was immunoprecipitated with anti C-terTnk1 (B) antibody from T47D and K562 cells, while t-Tnk1 was pulled down with anti pY$^{77}$ Tnk1 (A) antibody to perform the in vitro PTK activity assay. Tnk1 from T47D or K562 Y-phosphorylated Grb2, suggesting that it is in the latent form in the cells and could be activatable or induced to function as tumor suppressor. The t-Tnk1 showed none or weak Y-phosphorylation of Grb2 indicating that it is in the inactive dominant negative form.

In summary, the tyrosine kinase activity of Tnk1 is required for its tumor suppressor function in both mice (1, 4) and in human. Importantly, in human, the inventors have found loss of Tnk1 expression or its function occurring in lymphomas, liver, lung, breast, pancreas and other type of cancers (FIG. 2; Hoare et. al. unpublished data). Human cancer cell lines have been identified that do not express Tnk1, for example BIJAB, REH, CEM, Raji, A549 etc, from cell lines that express an inactive full length Tnk1 for example K562, T47D, MCF7, NCI H82, NCI H827, HEPG2 etc or truncated Tnk1 fusion gene products for example L540 (FIG. 2). Therefore, loss of Tnk1 may be a potential prognostic marker for early detection of cancers such as lymphomas, liver and lung in human. Hence, detection of inactive or kinase-dead Tnk1 (full length and truncated) or loss of Tnk1 expression, may serve as the diagnostic tool for the various forms of human cancer. Importantly, since the inventors have found that the full-length Tnk1 expressed in T47D, K562 and NCI H82 cell lines, possess PTK activity towards Grb2, under in vitro condition, when used as substrate (FIG. 3) that activation of the latent inactive Tnk1 may be an ideal strategy for cancer therapy.

Therapeutic Implications of Examples:

In humans, there is now growing evidence of expression of inactive or kinase-dead forms of Tnk1 in tumors cells. Recent evidence lead to the hypothesis that kinase-dead Tnk1 may function as promoter of tumor growth/metastasis, while Tnk1 expressed as a latent inactive kinase, due to post-translational modification through acetylation or scaffolding proteins in tumor cells, can be activated to induce apoptosis and destroy the tumor mass from within. Hence, use of anti Tnk1 antibodies and/or Tnk1 specific small molecule(s), Tnk1 siRNA or re-expression of wild type Tnk1 by reversing epigenetic silencing, may serve as pivotal therapeutic strategies. Since anti C-ter Tnk1 antibody (Antibody B) can efficiently interact and immuno-precipitate endogenous Tnk1 from K562 or T47D cells without interfering with its PTK activity (FIG. 3), it is hypothesized that the $F(ab)_2$ fragment of the anti C-ter Tnk1 antibody can efficiently activate the Tnk1's tumor suppressor function in tumors where Tnk1 is expressed, but is in its latent inactive form.

Diagnostic: ELISA Based Assay for the Detection of Loss Functional Tnk1.

It is well documented that the protein tyrosine kinase activity of PTKs is regulated by the phosphorylation/dephosphorylation of tyrosine residues present in its kinase and/or extracatalytic domains (10). Importantly, the PTK activity of Tnk1 point-mutants on Grb2 or STAT1 revealed the importance and functionality of the critical tyrosine (Y) site(s). It has been found that Tnk1 protein kinase activity is reduced when $Y^{77}$, $Y^{235}$, $Y^{277}$ or $Y^{287}$ is replaced with phenylalanine (F) (FIG. 2). This indicates that by measuring the loss of Tnk1 Y-phosphorylation at these sites, specifically $Y^{77}$, using phospho-specific antibody (Antibody A), may serve as the diagnostic markers for loss of Tnk1 function in human tumors. In the case of the truncated Tnk1-C17ORF61 fusion protein (tTnk1), though kinase-dead, is expressed in L540 as a Y-phosphorylated protein (at the mentioned Y-sites) and functions a tumor promoter (9; Hoare et al. unpublished data). We found that tTnk1 can be Y-phosphorylated in L540 cells by Src family kinases, namely Lyn (Hoare et al. unpublished data). Therefore, use of a phospho-specific antibody as a diagnostic marker will yield false positive results in the case of Tnk fusion protein(s). To overcome this limitation, size determination of the expressed Tnk1 in tumor cells becomes important to distinguish between full length and truncated Tnk1 proteins for the development of precision diagnostic tools for the early detect of cancer.

Two highly reactive antibodies have been generated. One against a 13 AA Tnk1 peptide phosphorylated at $Y^{77}$ (Antibody A), while the other against a 13AA Tnk1 C-terminal peptide (Antibody B). The antibody A can detect phosphorylated $Y^{77}$ present in full length Tnk1 or in the known truncated Tnk fusion protein (t-Tnk1), while antibody B detects only the full length Tnk1 but not t-Tnk1. Hence, both anti Tnk1 antibodies will be useful in the development of an ELISA based precision diagnostic kit for early detection of cancer. Initial data with lung, liver, breast cancer cell lines indicate complete loss of $Y^{77}$ phosphorylation, using antibody A, suggests that the expressed full length Tnk1, detected with antibody B in the cancer cell lines are functionally inactive (FIG. 2).

REFERENCES

1. Hoare S, Hoare K, Reinhard M, Lee Y J, Oh, P, May S. (2008) Tnk1/Kos1 knockout mice develop spontaneous tumors. Cancer Research 68, 8723-32.
2. Hoehn G T, Stokland T, Amin S, Ramirez M, et al. (1996). Tnk1, a novel intracellular tyrosine kinase gene isolated from human umbilical cord blood CD34+/Lin−/CD38− stem/progenitor cells. Oncogene, 12, 903-13.
3. Azoitei N, Brey A, Busch T, Fulda S, Adler G, Seufferlein T. (2007). Thirty-eight negative kinase1 (Tnk1) facilitates TNFα-induced apoptosis by blocking NF-κB activation. Oncogene 26, 6536-45.
4. May W S, Hoare K, Hoare S, Reinhard M K, Lee Y J, Oh S P. (2010). Tnk1/Kos1: A novel tumor suppressor. Trans Am Clin Climatol Assoc., 121, 281-92.
5. Hoare K, Hoare, S, Smith, O S, Kalmaz G, Small D, May S. (2003) Kos1, a nonreceptor tyrosine kinase that suppresses Ras signaling. Oncogene, 22, 3562-77.
6. Suk K, Kim S, Kim Y H, Kim K A, Chang I, Yagita H, Shong M, Lee M S. (2001). IFN-gamma/TNF-alpha synergism as the final effector in autoimmune diabetes: a key role for STAT1/IFN regulatory factor-1 pathway in pancreatic beta cell death. J Immunol. 166, 4481-89.
7. Thomas M, Finnegan C E, Rogers KM-A, Purcell J W, Trimble A, Johnston P G, Boland M P. (2004). STAT1: A modulator of chemotherapy-induced apoptosis. Cancer Research, 64, 8357-64.

8. Davis, H., Hunter C, Smith R et al. (2005) Somatic mutations of the protein kinase gene family in human lung cancer. Cancer Res. 65, 7591-5.
9. Gu T L, Chemy J, Tucker M, Wu J, Reeves C, Polakiewicz R D. (2010). Identification of activated Tnk1 kinase in Hodgkin's lymphoma. Leukemia. 24, 861-5.
10. Au-Yeung B B, Deindl S, Hsu L Y, Palacios E H, Levin S E, Kuriyan J, Weiss A (2009) The structure, regulation, and function of ZAP-70. Immunol Rev 228, 41-57.

It should be borne in mind that all patents, patent applications, patent publications, technical publications, scientific publications, and other references referenced herein and in the accompanying appendices are hereby incorporated by reference in this application to the extent not inconsistent with the teachings herein.

text, such embodiments are provided by way of example only, and not of limitation. Numerous variations, changes and substitutions will occur to those skilled in the art without materially departing from the invention herein. For example, the present invention need not be limited to best mode disclosed herein, since other applications can equally benefit from the teachings of the present invention. Also, in the claims, means-plus-function and step-plus-function clauses are intended to cover the structures and acts, respectively, described herein as performing the recited function and not only structural equivalents or act equivalents, but also equivalent structures or equivalent acts, respectively. Accordingly, all such modifications are intended to be included within the scope of this invention as defined in the following claims, in accordance with relevant law as to their interpretation.

```
                        SEQUENCE LISTING

<160> NUMBER OF SEQ ID NOS: 3

<210> SEQ ID NO 1
<211> LENGTH: 17
<212> TYPE: PRT
<213> ORGANISM: Homo sapiens

<400> SEQUENCE: 1

Glu His Lys Glu Pro Thr Leu Pro Ser Asp Ser Pro Arg His Leu Pro
1               5                   10                  15

Glu

<210> SEQ ID NO 2
<211> LENGTH: 18
<212> TYPE: PRT
<213> ORGANISM: Homo sapiens

<400> SEQUENCE: 2

Arg Glu Arg Leu Pro Trp Pro Lys Arg Lys Pro Pro His Asn His Pro
1               5                   10                  15

Met Gly

<210> SEQ ID NO 3
<211> LENGTH: 17
<212> TYPE: PRT
<213> ORGANISM: Homo sapiens

<400> SEQUENCE: 3

Lys Asn Trp Val Tyr Lys Ile Leu Gly Gly Phe Ala Pro Glu His Lys
1               5                   10                  15

Glu
```

It is important to an understanding of the present invention to note that all technical and scientific terms used herein, unless defined herein, are intended to have the same meaning as commonly understood by one of ordinary skill in the art. The techniques employed herein are also those that are known to one of ordinary skill in the art, unless stated otherwise. For purposes of more clearly facilitating an understanding the invention as disclosed and claimed herein, the following definitions are provided.

While a number of embodiments of the present invention have been shown and described herein in the present con-

What is claimed is:

1. An antibody that binds to an epitope of a region of Tnk1, wherein the region is selected from the group consisting of SEQ ID NO. 2 and SEQ ID NO. 3; and wherein the antibody that binds to an epitope contained within SEQ ID NO. 3 detects full length Tnk1 or truncated Tnk fusion protein (t-Tnk1) phosphorylated at Y77, wherein the antibody does not cross-react with phosphotyrosine itself, and the antibody that binds to an epitope contained within SEQ ID NO. 2 detects full length Tnk1 but not t-Tnk1.

2. The antibody of claim 1, wherein the antibody is a polyclonal antibody.

3. The antibody of claim 1, wherein the region is SEQ ID NO. 3.

4. The antibody of claim 1, wherein the region is SEQ ID NO. 2.

\* \* \* \* \*